(12) United States Patent
Chen et al.

(10) Patent No.: US 8,309,768 B2
(45) Date of Patent: Nov. 13, 2012

(54) FTY720-DERIVED ANTICANCER AGENTS

(75) Inventors: Ching-Shih Chen, Upper Arlington, OH (US); Samuel K. Kulp, Hillard, OH (US); Dasheng Wang, Dublin, OH (US); John C. Byrd, Columbus, OH (US); Natarajan Muthusamy, Galloway, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 13/305,927

(22) Filed: Nov. 29, 2011

(65) Prior Publication Data
US 2012/0136063 A1    May 31, 2012

Related U.S. Application Data

(60) Provisional application No. 61/417,566, filed on Nov. 29, 2010.

(51) Int. Cl.
*C07C 215/00* (2006.01)
*C07C 211/00* (2006.01)
*C07C 213/00* (2006.01)

(52) U.S. Cl. .......... 564/355; 564/336; 564/347

(58) Field of Classification Search ........... 564/336, 564/347, 355
See application file for complete search history.

(56) References Cited

U.S. PATENT DOCUMENTS

| | | | |
|---|---|---|---|
| 2,680,749 A | 6/1954 | Cawley et al. |
| 4,262,017 A | 4/1981 | Kulpers et al. |
| 4,751,224 A | 6/1988 | Agarwal et al. |
| 4,938,949 A | 7/1990 | Borch et al. |
| 6,004,565 A | 12/1999 | Chiba et al. |
| 6,121,329 A | 9/2000 | Fujii et al. |
| 6,417,223 B1 | 7/2002 | Sanders et al. |
| 6,476,004 B1 | 11/2002 | Sakai et al. |
| 6,645,998 B2 | 11/2003 | Sanders et al. |
| 6,703,384 B2 | 3/2004 | Sanders et al. |
| 6,770,672 B1 | 8/2004 | Sanders et al. |
| 6,858,227 B1 | 2/2005 | Lal et al. |
| 2004/0235938 A1 | 11/2004 | Sanders et al. |
| 2004/0248971 A1 | 12/2004 | Yeh et al. |
| 2005/0065149 A1 | 3/2005 | Wang et al. |
| 2005/0090520 A1 | 4/2005 | Lindquist |
| 2005/0215531 A1 | 9/2005 | Baumruker et al. |
| 2008/0009545 A1 | 1/2008 | Chen et al. |
| 2008/0161349 A1 | 7/2008 | Sanders et al. |
| 2009/0137530 A1 | 5/2009 | Kiuchi et al. |
| 2010/0022655 A1 | 1/2010 | Byrd et al. |
| 2010/0179216 A1 | 7/2010 | Kiuchi et al. |
| 2010/0267673 A1 | 10/2010 | Chen et al. |
| 2010/0267820 A1 | 10/2010 | Chen et al. |
| 2010/0273871 A1 | 10/2010 | Chen et al. |

FOREIGN PATENT DOCUMENTS

| | | |
|---|---|---|
| JP | 59-222415 | 12/1984 |
| WO | 01/58889 | 8/2001 |
| WO | 03/039461 | 5/2003 |
| WO | 2007/098139 | 8/2007 |
| WO | 2007/143081 | 12/2007 |
| WO | 2008/021532 | 2/2008 |
| WO | WO 2009119858 | * 10/2009 |
| WO | 2010/042998 | 4/2010 |
| WO | 2010/120711 | 10/2010 |
| WO | 2010/121111 | 10/2010 |

OTHER PUBLICATIONS

International Search Report for PCT/US2006/010882, mailed Feb. 9, 2007.
International Search Report and Written Opinion from PCT/US07/04337 dated Sep. 19, 2008.
International Search Report and Written Opinion from PCT/US07/12921 dated Dec. 12, 2007.
International Search Report and Written Opinion from PCT/US10/30799 dated May 18, 2010.
International Search Report and Written Opinion from PCT/US10/31363 dated Jul. 13, 2010.
Interview Summary from U.S. Appl. No. 11/708,792 dated Apr. 9, 2009.
Office action from U.S. Appl. No. 11/708,792 dated Jul. 6, 2009.
Response to Office action from U.S. Appl. No. 11/708,792 dated Aug. 12, 2009.
Office action from U.S. Appl. No. 11/708,792 dated Nov. 27, 2009.
Notice of Abandonment from U.S. Appl. No. 11/708,792 dated Jun. 22, 2010.
Office action from U.S. Appl. No. 12/302,953 dated Oct. 18, 2011.
Response from U.S. Appl. No. 12/302,953 dated Jan. 17, 2012.
Notice of Allowance from U.S. Appl. No. 12/302,953 dated Apr. 23, 2012.
Office action from U.S. Appl. No. 12/761,504 dated Apr. 11, 2012.
Office action from Australian Application No. 2007217810 dated Aug. 16, 2011.

(Continued)

*Primary Examiner* — Jafar Parsa
(74) *Attorney, Agent, or Firm* — Calfee, Halter & Griswold LLP

(57) ABSTRACT

A number of FTY720-derived compounds with antitumor activity are described. These compounds include the compounds of formula I:

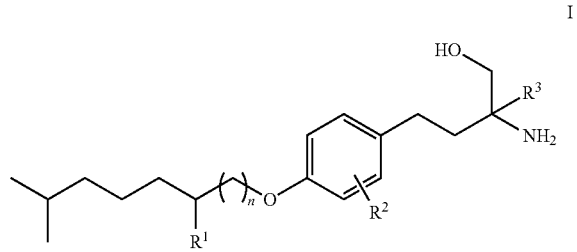

wherein $R^1$ is independently selected from the group consisting of hydrogen, methyl. methoxy, and hydroxyl; $R^2$ is independently selected from the group consisting of hydrogen, methoxy, and hydroxyl; $R^3$ is independently selected from the group consisting of alkyl and cyclo-alkyl; and n is independently selected from 0 to 6. The compounds have lower immunosuppressive side effects as a result of not being phosphorylated by sphingosine kinase 2.

16 Claims, 9 Drawing Sheets

OTHER PUBLICATIONS

Communication from European Application No. 07751119.4 dated Mar. 13, 2009.

Response from European Application No. 07751119.4 dated Feb. 17, 2010.

Extended European Search Report for European Application No. 07809273.1, dated Aug. 14, 2009.

Response to European Communication from 07809273.1 dated Sep. 22, 2010.

Arya P., et al., "Design and Synthesis of Analogs of Vitamin E: Antiproliferative Activity Against Human Breast Andenocarcinoma Cells", Bioiorganic & Medicinal Chemistry Letters, vol. 8, 1998, pp. 2433-2438.

Ayllon et al., "Protein Phosphatase 1 alpha is a Ras-activated Bad Phosphatase that regulated interleukin-2 deprivation-induced apoptosis", The EMBO Journal, 19, pp. 2237-2246 (2000).

Azuma et al., "Marked prevention of tumor growth and metastasis by a novel immunosuppressive agent, FTY720, in mouse breast cancer models", Cancer Research, 62: 1410-1419 (2002).

Azuma et al. "Selective cancer cell apoptosis induced by FTY720; evidence for a Bol-dependent pathway and impairment in ERK activity", Anticancer Research, 23: 3183-3193 (2003).

Bakin et al., "Attenuation of Ras signaling restores androgen sensitivity to hormone-refractory C4-2 prostate ancer cells", Cancer Res. 63, pp. 1975-1980 (2003).

Bang et al., "Activation of PKC but not of ERK is required for vitamin E-succinate-induced apoptosis of HL-60 cells", Biochem Biophys Res. Commun, 288, pp. 789-797 (2001).

Barnett, et al., "Vitamin E succinate inhibits colon cancer liver metastases", J Surg Res 106, pp. 292-298 (2002).

Baumhoer et al., "Glypican 3 expression in human nonneoplastic, preneoplastic, and neoplastic tissues", Am J Clin Pathol, 129, pp. 899-906 (2008).

Bellosillo et al., "Involvement of CED-3/ICE proteases in the apoptosis of B-chronic lymphocytic leukemia cells", Blood, 89: 3378-3384 (1997).

Birringer et al., "Vitamin E analogues as inducers of apoptosis: structure-function relation", Br J Cancer 88, pp. 1948-1955 (2003).

Boehler et al., "FTY720 alters the composition of T-lymphocyte subpopulations in the peripheral blood compartment of renal transplant patients", Transplantation Proceedings, 34: 2242-2243 (2002).

Bohler et al., "Pharmacodynamics of FTY720, the first member of a new class of immune-modulating therapeutics in transplantation medicine", International Journal of Clinical Pharmacology and Therapeutics, 41: 482-487 (2003).

Bohler et al., "FTY720 mediates apoptosis-independent lymphopenia in human renal allograft recipients: different effects on CD62L+ and CCR5+ T lymphocytes", Transplantation, 77: 1424-1432 (2004).

Braun, W.E. "Renal transplantation: basic concepts and evolution of therapy. J Clin Apher, 18: 141-152, 2003."

Brinkmann, V., "FTY720 alters lymphocyte homing and protects allografts without inducing general immunosuppression", Transplantation Proceedings, 33: 530-531 (2001).

Brinkmann et al., "The immune modulator FTY720 targets sphingosine 1-phosphate receptors", The Journal of Biological Chemistry, 277: 21453-21457 (2002).

Brinkmann, et al., "FTY720: targeting G-protein-coupled receptors for sphingosine 1-phosphate in transplantation and autoimmunity", Current Opinion in Immunology, 14: 569-575 (2002).

Brinkmann et al., "FTY720: sphingosine 1-phosphate receptor-1 in the control of lymphocyte egress and endothelial barrier function", American Journal of Transplantation; 4: 1019-1025 (2004).

Brinkmann, V. "FTY720: mechanism of action and potential benefit in organ transplantation", Yonsei Medical Journal, 45: 991-997 (2004).

Budde et al., First human trial of FTY720, a novel immunomodulator, in stable renal transplant patients. Journal of the American Society of Nephrology: JASN, 13: 1073-1083, 2002.

Budde et al., "Pharmacodynamics of single doses of the novel immunosuppressant FTY720 in stable renal transplant patients", American Journal of Transplantation: 3: 846-854 (2003).

Calabresi, et al., "Section IX Chemotherapy of Neoplastic Diseases—Introduction", Goodman & Gilman's The Pharmacological Basis of Theapeutics 10th ed. Hardman. et al., Eds, McGraw-Hill, NY, pp. 1361, 1383-1385 and 1388, (2001).

Carbrera et al., "Review article: the management of hepatocellular carcinoma", Allment, Pharmacol. Ther. 31, pp. 461-476 (2010).

Cattan, et al., "The C.B. 17 soid mouse strain as a model for human disseminated leukaemia and myeloma in vivo. Leukemia Research, 18:513-522, 1994".

Cheson et al., "National Cancer Institute-sponsored Working Group guidelines for chronic lymphocytic leukemia: revised guidelines for diagnosis and treatment: Blood, 87: 4990-4997, 1996".

Cheson et al., "Myelodysplastic syndromes standardized response criteria: further definition, Blood, 98; 1985, 2001."

Chiang et al., "Protein Phosphatase 2A acivates the proapoptotic function of BAD in interleukin- 3-dependent lymphoid cells by a mechanism requiring 14-3-3 dissociation", Blood, 1289-1297 (2001).

Chiba et al., "FTY720, a novel immunosuppressant possessing unique mechanisms. I. Prolongation of skin allograft survival and synergistic effect in combination with cyclosporine in rats", Transplantation Proceedings, 28, pp. 1056-1059 (1996).

Chua et al., "FTY720, a fungus metabolite, inhibits in vivo growth of androgen-independent prostate cancer", International Journal of Cancer, 117: 1039-1048 (2005).

Chuang et al., "Phosphorylation by c-Jun NH2-terminal kinase 1 regulates the stability of transcription factor Sp1 during mitosis", mol Biol Cell 19, pp. 1139-1151 (2008).

Chueh et al., "Induction of tolerance toward rat cardiac allografts by treatment with allochimeric class I MHC antigen and FTY720, Transplantation, 64: 1407-1414, 1997."

Chrispen et al., "Vitamin E succinate inhibits NF-KappaB and prevents the development of a metastatic phenotype in prostate cancer calls: implications for chemoprevention", Prostate, 67, pp. 582-590 (2007).

Cohen et al., "Oral fingolimod or intramuscular interferon for relapsing multiple sclerosis", N Engl J Med 362. pp. 402-415 (2010).

D'Costa et al., "The proapoptosis tumor suppressor protein kinase C-δ is lost in human squamous cell carcinomas", Oncogene 25, pp. 378-386 (2006).

Dalen et al., "Alpha-tocopheryl succinate sensitises a T lymphoma cell line to TRAIL-induced apoptosis by suppressing NF-kappB activation", Br. J cancer 88, pp. 153-158 (2003).

Degterev et al., "Identification of small-molecule inhibitors of interaction between the BH3 domain and Bol-x", Nat. Cell Biol, 3, pp. 173-182 (2001).

Dong et al., "Vitamin E analogues inhibit anglogenesis by selective induction of apoptosis proliferating endothelial cells: the role of oxidative stress", Cancer Res 67, pp. 11906-11913 (2007).

Dragun et al., "FTY720: early clinical experience. Transplantation Proceedings, 36: 544S-548S, 2004".

Dragun et al., "FTY720-induced lymphocyte homing modulates post-transplant preservation/reperfusion injury", Kidney Int 65, pp. 1076-1083 (2004).

Enosawa et al., "Induction of selective cell death targeting on mature T-lymphocytes in rats by a novel immunosuppressant, FTY720", Immunopharmacology, 34: 171-179 (1996).

Feschenko et al., "A novel cAMP-stimulated pathway in protein phosphatase 2A activation", J. Pharmacol. Exp. Ther. 302, pp. 111-118 (2002).

Ferguson, R., "FTY720 immunomodulation: optimism for improved transplant regimens. Transplantation Proceedings, 36: 549S-553S, 2004".

Fujino, et al., "Activation of caspases and mitochondria in FTY720-mediated apoptosis in human T cell line Jurkat", International Immunopharmacology, 1:2011-2021 (2001).

Fujino et al., "Distinct pathways of apoptosis triggered by FTY720, etoposide, and anti-Fas antibody in human T-lymphoma cell line (Jurkat cells)", Journal of Pharmacology and Experimental Therapeutics, 300, p. 939-945 (2002).

Genini et al., "Nucleotide requirements for the in vitro activation of the apoptosis protein-activating factor-1-mediated caspase pathway. The Journal of Biological Chemistry, 275:29-34, 2000".

Gu et al., "Vitamin E succinate induces ceramide-mediated apoptosis in head and neck squamous cell carcinoma in vitro and in vivo", Clin Cancer Res, 14, pp. 1840-1848 (2008).

Hahn et al., "Dietary administration of the proapoptotic vitamin E analogue alpha-tocopheryloxyacetic acid inhibits metastatic murine breast cancer". Cancer Res 66, pp.9374-9378 (2006).

Ho et al., "Effects of a novel immunomodulating agent, FTY720, on tumor growth and angiogenesis in hepatocellular carcinoma", Molecular Cancer Therapeutics, 4: 1430-1438 (2005).

Hoshino et al., "FTY720, a novel immunosuppressant possessing unique mechanisms. II. Long-term graft survival induction in rat heterotopic cardiace allografts and synergistic effect in combination with cyclosporine A", Transplantation Proceedings, 28: pp. 1060-1061 (1996).

Huang et al., "a-Tocopheryl succinate and derivatives mediate the transcriptional repression of a androgen receptor in prostate cancer cells by targeting the PP2A-JNK-Sp1 Signaling axis", Carcinogenesis, vol. 30, No. 7, pp. 1125-1131, 2009.

Hung et al., FTY720 induces apoptosis in hepatocellular carcinoma cells through activation of protein kinase Cδ signaling, Cancer Res 68, pp. 1204-1212 (2008).

Jackson et al., "The enigmatic protein kinase Cδ: complex roles in cell proliferation and survival", FASEB J, 18, pp. 627-636 (2004).

Janssens et al., "Protein phosphatase 2A: a highly regulated family of serine/threonine phosphatases implicated in cell growth and signalling", Biochem J, 353, pp. 417-439 (2001).

Johnson et al., "A novel celecoxib derivative, OSU03012, induces cytotoxicity in primary CLL cells and transformed B-cell lymphoma cell line via a caspase- and Bcl-2-independent mechanism", Blood, v. 105, p. 2504-2509 (2006).

Juntilla et al., "CIP2A inhibits PP2A in human malignancies", Cell, 130, pp. 51-62 (2007).

Kahan et al., "Pharmacodynamics, pharmacokinetics, and safety of multiple doses of FTY720 in stable renal transplant patients: a multicenter, randomized, placebo-controlled, phase I study. Transplantation, 76: 1079-1084, 2003".

Kawaguchi et al., "FTY720, a novel immunosuppressant possessing unique mechanisms. III. Synergistic prolongation of canine renal allograft survival in combination with cyclosporine A", Transplantation Proceedings 28: pp. 1062-1063 (1996).

Kitada et al. "Expression of apoptosis-regulating proteins in chronic lymphocytic leukemia: correlations with In vitro and In vivo chemoresponses", Blood, 91: 3379-3389 (1998).

Kiuchi et al., "Synthesis and immunosuppressive activity of 2-substituted 2-aminopropane-1, d-diols and 2-aminoethanols", J Med Chem 43, pp. 2946-2961 (2000).

Kogure et al., "Potentiation of anti-cancer effect by intravenous administration of vesiculated tocophyeryl hemisuccinate on mouse melamona in vivo", Cancer Lett, 192, pp. 19-24 (2003).

Koopman et al., Annexin V for flow cytometric detection of phosphaticiylserine expression on B cells undergoing apoptosis. Blood, 84: 1415-1420, 1994.

Lawson et al., "Novel vitamin E analogue decreases syngeneic mouse mammary tumor burden and reduces lung metastasis", Mol Cancer Ther, 2, pp. 437-444 (2003).

Lee et al., "FTY720 induces apoptosis of human hepatoma cell lines through PI3-K-mediated Akt dephosphorylation", Carcinogenesis, 25: 2397-2405 (2004).

Lee et al., "Significance of the Rac signaling pathway in HCC cell motility: implications for a new therapeutic target", Carcinogenesis, 26: 681-687 (2005).

Lee et al., "FTY720: a promising agent for treatment of metastatic hepatocellular carcimona. Clinical Cancer Research: an Official Journal of the American Association for Cancer Research", 11: 8456-8466 (2005).

Lei et al., "The Bax subfamily of Bcl2-related proteins is essential for apoptotic signal transduction by c-Jun NH(2)-terminal kinase", Mol Cell Biol, 22, pp. 4929-4942 (2002).

Li et al., "The myeloid leukemia-associated protein SET is a potent inhibitor of protein phosphatase 2A", J. Biol. Chem. 271, pp. 11059-11062 (1996).

Li et al., "Induction of lymphocyte apoptosis by a novel immunosuppressant FTY720: relation with Fas, Bcl-2 and Bax expression", Transplantation Proceedings, 29: 1267-1268 (1997).

Li Dengju et al., "Role of extracellular regulated protein kinases in FTY720-induced apoptosis of leukemia cell lines HL-60 and U937", Journal of Huazhong University of Science and Technology [Med Sci], 24, p. 45-47 (2004).

Liu, "Small molecule antagonists of LFA-1/ICAM-1 interactions as potential therapeutic agents", Expert Opinion Ther. Patents, 11 (9): pp. 1383-1393 (2001).

Llovet et al., "Sorafenib in advanced hepatocellular carcinaoma", N Engl J Med, 359 pp. 378-390 (2008).

Lugovskoy et al., "A Novel approach for characterizing protein ligand complexes: Molecular basis for specificity of small-molecule Bct-2 inhibitors", J Am Chem Soc, 124, pp. 1234-1240 (2002).

Malafa et al., "Vitamin E Succinate promotes breast cancer tumor dormancy", J Surg Res, 93, pp. 163-170 (2000).

Malafa et al., "Inhibition of Angiogenesis and promotion of melanoma dormancy by vitamin E succinate", Ann Surg Oncol 9, pp. 1023-1032 (2002).

Martin, R., "Closing in on an oral treatment" Multiple Sclerosis, Nature 464, pp. 360-362 (2010).

Masubuchi et al., "FTY720, a novel immunosuppressant, possessing unique mechanisms. IV, Prevention of graft versus host reactions in rats, Transplantation Proceedings, 28: 1064-1065, 1996".

Matsuoka et al., "Reduction of phosphorylated Akt/PKB by immunosuppressant FTY720" Cell Biology Internationa, 24, p. 976-977 (2000).

Matsuoka et al, "A novel immunosuppressive agent FTY720 induced Akt dephosphorylation in leukemia cells", British Journal Pharmacology, 138: 1303-1312 (2003).

McConkey, et al., "Apoptosis sensitivity in chronic lymphocytic leukemia is detrmined by endogenous endonuclease content and relative expression of BCL-2 and BAX", J. Immunol. 156: pp. 2624-2630 (1996).

Moon et al., "PDE4 inhibitors activate a mitochondrial apoptotic pathway in chronic lymphocytic leukemia cells that is regulated by protein phosphatase 2A", Blood 101, pp. 4122-4130 (2003).

Morley et al., "Proteasome inhibitors and immunosuppressive drugs promote the cleavage of eIF4GI and eIF4GII by caspase-8-independent mechanisms in Jurkat T cell lines" FEBS Letters, 503: 206-212 (2001).

Mullershausen et al., ":ersistent signaling induced by FTY720-phosphate is mediated by internalized S1P1 receptors", Nat Chem Biol 5, pp. 428-434 (2009).

Mumby, M., "PP2A: unveiling a reluctant tumor suppressor", Cell, 130, pp. 21-24 (2007).

Nagahara et al., "Evidence that FTY720 induces T cell apoptosis in vivo", Immunopharmacology, 48: 75-85 (2000).

Nagahara et al., "Immunosuppressant FTY720 induces apoptosis by direct induction of permeability transition and release of cytochrom c from mitochondria", Journal of Immunology, 165, p. 3250-3259 (2000).

Nagahara et al., "Coordinate involvement of cell cycle arrest and apoptosis strengthen the effect of FTY720", Japanese Journal of Cancer Research: 92: 680-687 (2001).

Nagahara et al., "T cell selective apoptosis by a novel immunosuppressant, FTY720, is closely regulated with Bcl-2", British Journal of Pharmacology, 137: 953-762 (2002).

Neuzil et al., "Induction of cancer cell apoptosis by alpha-tocopheryl succinate: molecular pathways and structural requirements", FASEB J, 15, pp. 403-415 (2001).

Neuzil et al., "Selective cancer cell killing by tocopheryl succinate", Br. J. Cancer, 84, pp. 87-89 (2001).

Neuzil et al., "a-Tocopheryl succinate epitomizes a compound with a shift in biological activity due to pro-vitamin-to-vitamin conversion", Biochem Biophys Res Commun, 293, pp. 1309-1313 (2002).

Neuzil et al., "Vitamin E analogs, a novel group of "mitocans," as anticancer agents: the importance of being redox-silent", Mol Pharmacol, 71: pp. 1185-1199 (2007).

Ni et al., "Vitamin E succinate inhibits human prostate cancer cell growth via modulation cell cycle regulatory machinery", Biochem Biophys Res Commun, 300, pp. 357-363 (2003).

Omar et al., "Targeting of the Akt-nuclear factor-kB signaling network by [1-(4-chloro-3-nitrobenzenesulfonyl)-1H-indol-3-yl]-methanol (OSU-A9), a novel indole-3-carbinol derivative, in a mouse model of hepatocellular carcinoma", Mol Pharmacol 76, pp. 957-968 (2009).

Pabst et al., "Enhanced FTY720-mediated lymphocyte homing requires G alpha I signaling and depends on beta 2 and beta 7 integrin", J. Immunol, 176: 1474-1480 (2006).

Prasad et al., "Effects of tocopherol (Vitamin E) acid succinate on morphological alterations and growth inhibition in melanoma cells in culter", Cancer Res 42, pp. 550-555 (1982).

Prasad et al., "a-Tocopheryl succinate, the most effective form of vitamin E for adjuvant cancer treatment: A review", J Am Coll Nutr 22, pp. 108-117 (2003).

Prieschl, "The balance between sphingosine and sphingosine-1-phosphate is decisive for mast cell activation after Fce receptor I triggering", J Exp Med 190, pp. 1-8 (1999).

Qian et al., "c-Jun involvement in vitamin E succinate induced apoptosis of reticuloendotheliosis virus transformed avian lymphoid cells", Oncogene 15, p. 223-230 (1997).

Quesniaux et al, "The novel immunosuppressant FTY720 induces peripheral lymphodepletion of both T- and B-cells in cynomolgus monkeys when given alone, with Cyclosporine Neoral (R) or with RAD", Transplant Immunology, 8: 177-187 (2000).

Reno et al., "Analysis of protein kinase C delta (PKCö) expression in endometrial tumors", Hum Pathol, 39, pp. 21-29 (2008).

Reyland, "Protein kinase Cö and apoptosis", Biochem Soc Trans 35, pp. 1001-1004 (2007).

Salesse et al., "BCR/ABL-mediated increased expression of multiple known and novel genes that may contribute to the pathogenesis of chronic myelogenous leukemia", Molecular Cancer Therapeutics, v. 2, p. 173-182 (2003).

Schonthal, A. H., "Role of Serine/threonine protein phosphatase 2A in cancer", Cancer Lett. 170, pp. 1-13 (2001).

Seitz et al., "Effects of sphingoine 1-phosphate (S1P) and expression of S1P receptors in chronic lymphocyte leykemia (B-CLL): potential role in cell trafficking and survival", Experimental Hemaology, 33, p. 99 (2005).

Shanker et al., "Vitamin E succinate in combination with mda-7 results in enhanced human ovarian tumor cell killing through modulation of extrinsic and intrinsic apoptolic pathways", Cancer Lett, 254, pp. 217-226 (2007).

Shiau et al., "a-tocopheryl succinate induces apoptosis in prostate cancer cells in part through inhibition of Bcl-xL/Bcl-2 function", J Biol Chem, 281, pp. 11819-11825 (2006).

Skerjanec et al., "FTY720, a novel immunomodulator in de novo kidney transplant patients: pharmacokinetics and exposure-response relationship. Journal of Clinical Pharmacology, 45: 1268-1278, 2005".

Stoetzer et al., "Drug-induced apoptosis in chronic lymphocytic leukemia. Leukemia: Official Journal of the Leukemia Society of America, Leukemia Research Fund, U.K. 13: 1873-1880, 1999".

Suleiman et al., "FTY720 prevents renal T-cell infiltration after ischemia/reperfusion injury, Transplantation Proceedings, 37: 373-374, 2005".

Suzuki et al., "A new immunosuppressant, FTY720, induces bcl-2-associated apoptotic cell death in human lymphocytes", Immunology, 89: 518-523 (1996).

Suzuki et al., "A novel immunosuppressant FTY720, with a unique mechanism of action, induces long-term graft acceptance in rat and dog allotransplantation", Transplantation, 61: pp. 200-205 (1996).

Suzuki et al., "Long-tern graft acceptance in allografted rats and dogs by treatment with a novel immunosuupressant, FTY720. Transplantation Proceedings, 28: 1375-1376, 1996."

Suzuki et al., "Induction of lymphocyte apoptosis and prolongation of allograft survival by FTY720. Transplantation Proceedings, 26: 2049-2050, 1996."

Suzuki et al., "Immunosuppressive effect of a new drug, FTY720, on lymphocyte responses in vitro and cardiac allograft survival in rats. Transplant Immunology, 4: 252-255, 1996."

Takabe et al., ""Inside-out" signaling of sphingosine-1-phosphate: therapeutics targets", Pharmacol Rev 60, pp. 181-195 (2008).

Tchou et al., "GSTP1 CpG island DNA hypermethylation in hepatocelluar carcinomas", Int J Onjcol, 16, pp. 663-676 (2000).

Tedesco-Silva et al., "FTY720, a novel immunomodulator: efficacy and safety results from the first phase 2A study in de novo renal tranplantation. Transplantation. 77: 1826-1833, 2004."

Tedesco-Silva et al., FTY720, a novel immunomodulator: efficacy and safety results from the first phase 2A study in de novo renal transplantation. Transplantation, 79: 1553-1560. 2005.

Thomas, et al., "Drug-induced apoptosis in B-cell chronic lymphocytic leukemia: relationship between p53 gene mutation and bct-2/bax proteins in drug resistance", Oncogene 12: pp. 1055-1062 (1996).

Thomas, et al., "Opportunities for Targeted Therapies in Hepatocellular carcinoma", J. Clin Oncol. 23, pp. 8093-8108 (2005).

Tseng et al., "Overcoming trastuzumab resistance in HER2-overexpressing breast cancer cells by using a novel celecoxib-derived phosphoinositide-dependent kinase-1 inhibitor", Mol Pharmacol 70, pp. 1534-1541 (2006).

Varga et al., "Tumor grade-dependent alterations in the protein kinase C isoform pattern in urinary bladder carcinomas", Eur Urol 40, pp. 402-405 (2004).

Wang et al., "Repression of Androgen Receptor in Prostate Cancer Cells by phenethyl isothiocyanate" Carcinogenesis, 27, pp. 2124-2132 (2006).

Wang et al., "Vitamin E analogues as anticancer agents: lessons from studies with alpha-tocopheryl succinate", Mol. Nutr. Food Res., 50, pp. 675-685 (2006).

Wang et al., "A peptide conjugate of vitamin E succinate target breast cancer cells with high ErbB2 expression", Cancer Res 67, pp. 3337-3344 (2007).

Wang et al., "a-Tocopheryl succinate as a scaffold to develop potent inhibitors of breast cancer cell adhesion", J Med Chem 52, pp. 5642-5648 (2009).

Weber et al., "Induction of cancer cell apoptosis by alpha-tocopheryl succinate: molecular pathways structural requirements", FASEB, J., 15 (2) Feb. 2001.

Weber et al., "Vitamin E succinate is a potent novel antineoplastic agent with high selectivity and cooperativity with tumor necrosis factor-related apoptosis-inducing ligang (Apo2 ligand) in vivo", Clin Cancer Res 8, pp. 863-869 (2002).

Weber et al., "Mitochondria play a central role in apoptosis induced by alpha-tocopheryl succinate, an agent with antineoplastic activity: comparis with receptor-mediated pro-apoptosis signaling", Biochemistry, 42, pp. 4277-42941 (2003).

Wu et al., "Cellular and molecular effects of alpha-tocopheryloxybutyrate: Lessions for the designs of vitamin E analog for cancer prevention", Anticander Research, Helenic Anticancer Institute, Athens, vol. 24, No. 6, Nov. 1, 2004, pp. 3795-3802.

Yasui et al., "FTY720 induces apoptosis in multiple myeloma cells and overcomes drug resistance", Cancer Research, 65: 7476-7484 (2005).

Yin et al., "The therapeutic and preventive effect of RRR-alpha-vitamin E succinate on prostate cancer via induction of insulin-like growth factor binding protein-3", Clin Cancer Res, 13, pp. 2271-2280 (2007).

You et al., "RRR-alpha-tocopheryl succinate induces MDA-MB-435 and MCF-7 human breast cancer cells to undergo differentiation", Cell Growth Differ, 12, pp. 471-480 (2001).

You et al., "Role of extracellular signal-regulated kinase pathway in RRR-alpha-tocopheryl succinate-induced differentiation of human MDA-MD-435 breat cancer cells", Mol Carcinog, 33, pp. 228-236 (2006).

Yu et al., "Activation of extracellular signal-regulated kinase and c-Jun-NH(2)-terminal kinase but not p38 mitogen-activiated protein kinases is required for RRR-alpha-tocopheryl succinate-induced apoptosis of human breast cancer cells", Cancer Res 61, pp 6569-6576 (2001).

Tusof et al., "Immunohistochemical expression of π class glutathione S-transferase and α-Fetoprotein in hepatocellular carcinoma and chronic liver disease", Anal Quant Cytol Histol, 25, pp. 332-338 (2003).

Zhang et al., "Vitamin E succinate inhibits the fuction of androgen receptor and expression of prostate-specific antigen in prostate cancer cells", Proc Natl Acad Sci USA, 99, pp. 7408-7413 (2003).

Zhao et al., "alpha-tocopheryl succinate-induced apoptosis in human gastric cancer cells is modulated by ERK1/2 and c-Jun N-terminal kinase in a biphase manner", Cancer Lett, 247, pp. 346-352 (2007).

Zhou et al., "FTY720, a fungus metabolite, inhibits invasion abiltiy of androgen-independent prostate cancer cells through inactivation of RhoA-GTPase", Cancer Letters, 233: 36-47 (2006).

International Search Report and Written Opinion from PCT/US11/62304 dated Jun. 28, 2012.

Search Report from European Application No. 10765245.5 dated Jul. 11, 2012.

* cited by examiner

Synthetic Scheme

FTY720-DERIVED ANTICANCER AGENTS

CROSS REFERENCE TO RELATED APPLICATIONS

This application claims priority to, and any other benefit of U.S. Provisional Application No. 61/417,566, filed on Nov. 29, 2010, which is hereby incorporated by reference in its entirety.

GOVERNMENT FUNDING

The present invention was supported by Public Health Service Grants R21CA133710 and R01 CA112250 from the National Cancer Institute of the National Institutes of Health. The Government has certain rights in this invention.

BACKGROUND

Hepatocellular carcinoma (HCC) is a leading cause of cancer death worldwide, and is expected to become more prevalent in the US over the next decade due to the dramatic rise in the incidence of hepatitis C virus infection. The most effective way to treat most cancerous tumors is by surgically removing them. Unfortunately, many subjects with hepatocellular carcinoma aren't candidates for surgery due to the size or location of the tumor, the existence of significant liver cirrhosis, or because the tumor has grown into the blood vessels. It would therefore be very useful to obtain a drug that would be effective against HCC.

A major challenge in the systemic treatment of HCC is cellular resistance to conventional cytotoxic agents, which may be attributed to the heterogeneity of genetic abnormalities acquired during the course of hepatocarcinogenesis. Traditional systemic chemotherapy of hepatocellular carcinoma has thus demonstrated poor results. Cabrera et al., Aliment. Pharmacol. Ther. 31, 461-476 (2010). Targeting molecular defects that allow HCC cells to evade apoptosis signaling consequently represents a viable strategy to improve patient outcome. Accordingly, a number of therapeutic agents targeting aberrant cellular growth and survival signaling pathways have been investigated for the treatment of HCC. Thomas et al., J Clin Oncol, 23, 8093-8108 (2005) Recently, sorafenib, a multi-kinase inhibitor, was approved for the treatment of advanced HCC. Llovet et al., N Engl J. Med., 359, 378-390 (2008) This therapy, however, only works in a subset of patients and is not curative, which underlies the urgency for identifying new therapies.

FTY720 is a synthetic sphingosine immunosuppressant that was recently approved for the treatment of relapsing multiple sclerosis. Cohen et al., N Engl J. Med., 362, 402-415 (2010). Evidence indicates that the immunosuppressive effect of FTY720 is attributable to the ability of its phosphorylated metabolite (p-FTY720) to induce T lymphocyte homing by targeting sphingosine-1-phosphate (S1P) receptors. Takabe et al., Pharmacol Rev., 60, 181-195 (2008) Recent studies indicate that FTY720 induces apoptosis and inhibits angiogenesis and metastasis in HCC, suggesting its translational potential as a cancer therapeutic agent. Lee et al., Carcinogenesis, 25, 2397-2405 (2004); Hung et al., Cancer Res, 68, 1204-1212 (2008). However, in addition to side effects common to immunomodulatory therapy, FTY720 was reported to cause cardiovascular complications, macular oedema, and brain inflammation, which may be due to FTY720 interacting with more than one S1P-receptor subtypes. Martin R., Nature, 464, 360-362 (2010). Accordingly, there remains a need for the development of more effective FTY720 derivatives.

SUMMARY OF THE INVENTION

Based on the inventors' finding that FTY720 mediates apoptosis in HCC cells by activating reactive oxygen species (ROS)-protein kinase Cδ signaling independent of effects on sphingosine-1-phosphate (S1P) receptors, they embarked on the pharmacological exploitation of FTY720 to develop a non-immunosuppressive analogue with antitumor activity. This effort led to the development of a number of compounds, including OSU-2S, which exhibits higher potency than FTY720 in suppressing HCC cell growth through PKCδ activation. In contrast to FTY720, OSU-2S was not phosphorylated by sphingosine kinase 2 (SphK2) in vitro, and did not cause S1P1 receptor internalization in HCC cells or T lymphocyte homing in immunocompetent mice. Though devoid of S1P1 receptor activity, OSU-2S exhibited higher in vitro antiproliferative efficacy relative to FTY720 against HCC cells without cytotoxicity in normal hepatocytes. Several lines of pharmacological and molecular genetic evidence indicate that ROS-PKCδ-caspase 3 signaling underlies OSU-2S-mediated antitumor effects, and that differences in the antitumor activity between FTY720 and OSU-2S were attributable to SphK2-mediated phosphorylation of FTY720, which represents a metabolic inactivation of its antitumor activity. Finally, OSU-2S exhibited high in vivo potency in suppressing xenograft tumor growth in both ectopic and orthotopic models without overt toxicity. In conclusion, using the molecular platform of FTY720, the inventors developed OSU-2S, a novel PKCδ-targeted antitumor agent, that is devoid of S1P1 receptor activity and is highly effective in suppressing HCC tumor growth in vivo.

DETAILED DESCRIPTION OF THE INVENTION

Figure 1:
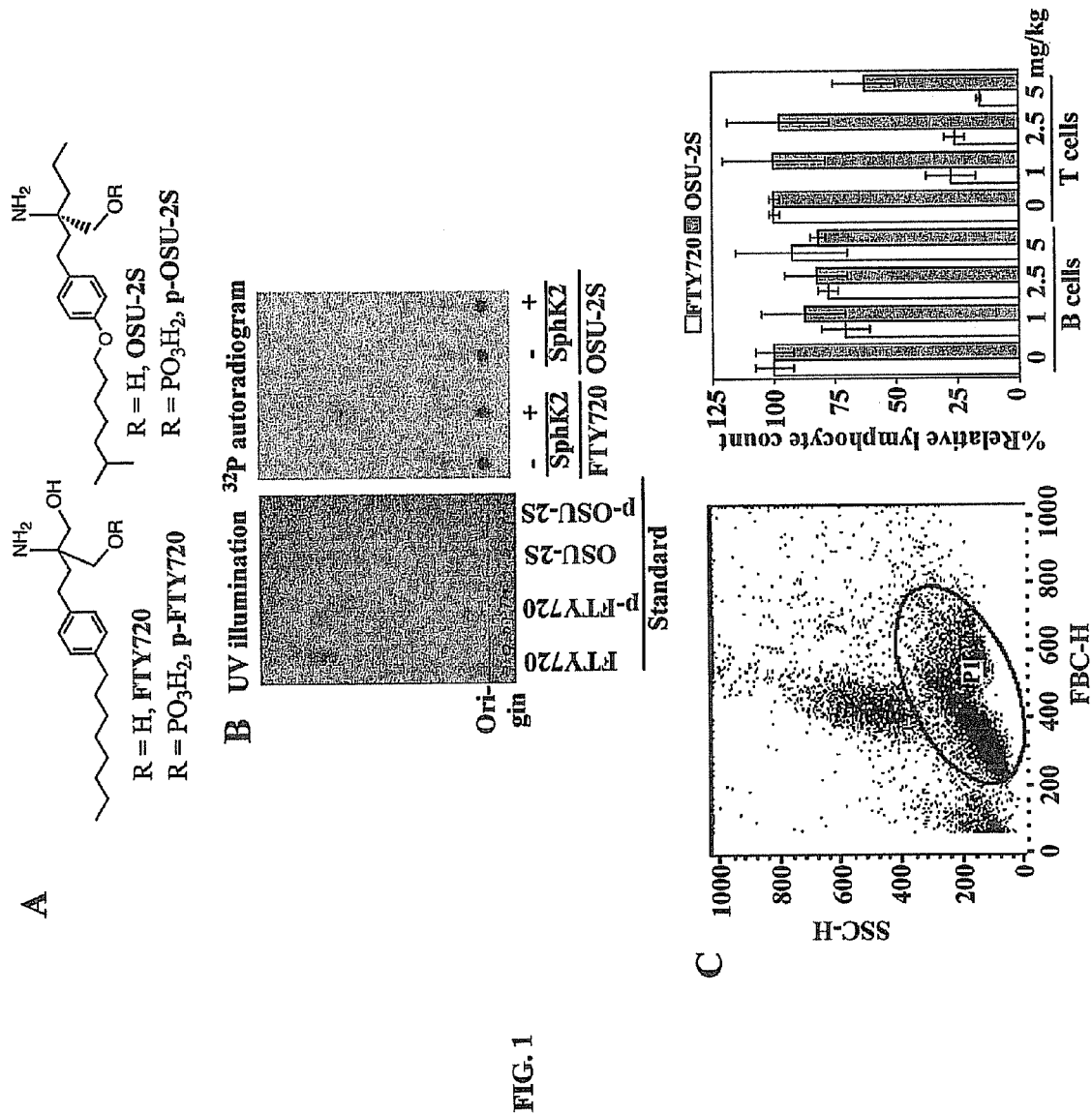
FIG. 1 provides structures, graphs, and data relating to the decreased immunosuppressive effects of FTY720-derived antitumor agents. Section (A) provides chemical structures of FTY720 and OSU-2S. Section (B) demonstrates that OSU-2S is not a substrate of sphingosine kinase 2 (SphK2). Left panel, thin-layer chromatogram of the standard compounds FTY-270, p-FTY720, OSU-2S, and p-OSU-2S, visualized by UV illumination. Right panel, autoradiogram of the reaction products from the incubation of FTY720 or OSU-2S with γ-32P-ATP in the presence (+) or absence (−) of recombinant SphK2 after separation by thin layer chromatography. Section (C) shows the results from flow cytometric analysis of numbers of lymphocytes in the peripheral blood collected from male CD2F1 mice 6 h after treatment with FTY720 or OSU-2S, at 1, 2.5, or 5 mg/kg, or vehicle via i.p. injection. Left panel, dot-plot shows the gating of the lymphocyte population as P1 based on forward and side-scatter profiles. Right panel, effect of FTY720 and OSU-2S relative to vehicle control on the numbers of circulating B and T-lymphocytes in the peripheral blood of immunocompetent CD2F1 mice at 6 h post-treatment. Columns, mean; bars, ±SD (n=3).

The present invention provides a number of FTY720-derived compounds with antitumor activity. These compounds can provide significant antitumor activity, while exhibiting decreased immunosuppression and other associated side effects as a result of their resistance to phosphorylation by sphingosine kinase 2. These compounds have been shown to be effective in treating cancer, including hepatocellular carcinoma, which exhibits resistance to many conventional antitumor agents.

DEFINITIONS

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

As used herein, the term "organic group" is used to mean a hydrocarbon group that is classified as an aliphatic group, cyclic group, or combination of aliphatic and cyclic groups (e.g., alkaryl and aralkyl groups). An alkaryl group is a an aryl group that is attached to the remainder of the structure by an intervening alkyl group, whereas an aralkyl group is an aryl group that is attached directly to the structure but that includes one or more additional alkyl groups attached thereto. In the context of the present invention, suitable organic groups for the compounds of the invention are those that do not interfere with the desired activity of the compounds (e.g., their anticancer activity). In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., $C_1$-$C_4$ alkyl groups are alky groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclobutyl, cyclobutylmethyl, cyclopentyl, and cyclohexyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo moieties include chlorine, bromine, fluorine, and iodine.

The term "aryl" as used herein includes carbocyclic aromatic rings or ring systems. The aryl groups may include a single aromatic ring, a plurality of separate aromatic rings, or a fused aromatic ring system. Carbocyclic aromatic rings do not include heteroatoms. Examples of aryl groups include phenyl, naphthyl, biphenyl, fluorenyl and indenyl. Aryl groups may be substituted or unsubstituted.

Unless otherwise indicated, the term "heteroatom" refers to the atoms O, S, or N. The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with one or more nonperoxidic O, N, S, or F substituents or other conventional substituents such as methyl groups. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. This is true regardless of whether or not the enantiomers are shown in chemical formula representing the compounds. For example, if a compound that includes a chiral center is shown without any indication of stereochemistry, it is presumed to represent all possible stereoisomers of the compound. It should be understood that the term "compound" includes any or all of such forms, whether explicitly stated or not (although at times, "salts" are explicitly stated).

Treat", "treating", and "treatment", etc., as used herein, refer to any action providing a benefit to a subject afflicted with a condition or disease such as cancer, including improvement in the condition through lessening or suppression of at least one symptom, delay in progression of the disease, etc.

Prevention, as used herein, refers to any action providing a benefit to a subject at risk of being afflicted with a condition or disease such as cancer, including avoidance of the development of cancer or a decrease of one or more symptoms of the disease should cancer develop. The subject may be at risk due to exposure to a carcinogen, or as a result of family history.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

One aspect of the invention provides a number of compounds that have been prepared, based on the FTY720 scaffold. These compounds include the compounds of formula I:

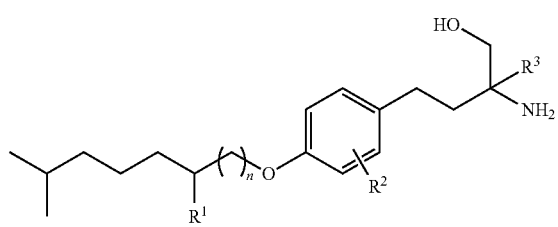

I wherein $R^1$ is independently selected from the group consisting of hydrogen, methyl. methoxy, and hydroxyl; $R^2$ is independently selected from the group consisting of hydrogen, methoxy, and hydroxyl; $R^3$ is independently selected from the group consisting of alkyl and cyclo-alkyl; and n is independently selected from 0 to 6. These compounds can be referred to as "aminoalkyl alcohol" compounds as a result of the sphingosine-related amine and alcohol functionality provided along one of the side-chains of these compounds. In addition, note that $R^2$, as shown in formula I above, can be provided at the either open position along the phenyl group; i.e., either the 2 or 3 position.

One or more of the substituents of the compounds of formula I can be varied to provide additional embodiments of the invention. The compounds can be varied at different regions of the compounds. For example, the compounds can be varied at the amino alcohol end of the compound by varying $R^3$. Alternately, or in addition, the compounds can be varied along the aromatic portion of the compound by varying the nature and position of $R^2$. Finally, the compounds can also be varied, again alternately or in addition, by varying n or $R^1$ of the alkyl group extending beyond the ether functionality.

With regard to the alkyl group, in some embodiments $R^1$ is hydrogen. These alky groups can be provided in a more limited size range by including n from 0 to 3. The alky groups can also include $R^1$ as a methyl moiety. These alkyl groups can also be provided in a more limited size range by including n from 0 to 3.

The phenyl group can also be modified by including varying $R^2$ substituents. For example, $R^2$ can be hydrogen such that the phenyl group is unsubstituted, outside of the alkyl and amino alcohol side chains. Alternately, $R^2$ can be a methoxy group at the 2 or 3 position, or a hydroxyl group at the 2 or 3 position along the phenyl ring.

The amino alcohol group of the compounds can also be varied to provide a number of different embodiments of the invention. In particular, the $R^3$ group can be varied to have various different alkyl or cycloalkyl groups. For example, in different embodiments, $R^3$ can be propyl, isopropyl, isobutyl, cyclopropyl methyl, or cyclobutyl methyl.

Finally, a preferred compound of the invention is OSU-2S, which has the structure:

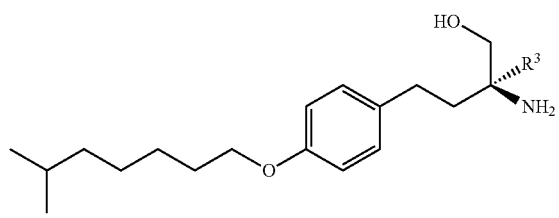

The structures and nomenclature of a number of the compounds of the invention are shown in the schemes and tables provided below. In the tables, the number of carbons in the "n" portion of the sidechain, as well as a full structure of the side chain, are shown to the left of the name of the compound. While the structures and nomenclature provided below are for the (S)-enantiomer, the (R) enantiomers are also considered to be within the scope of the present invention. Accordingly, one embodiment of the invention provides the compounds of Table 1:

TABLE I

Compounds wherein $R^1$ is hydrogen or methyl, $R^2$ is hydrogen, and $R^3$ is propyl.

| N & alkyl sidechain | Name |
| --- | --- |
| n = 0, | (S)-2-Amino-2-{2-[4-(7-methyl-hexyloxy)-phenyl]-ethyl}-butan-1-ol |
| n = 1, | (S)-2-Amino-2-{2-[4-(8-methyl-heptyloxy)-phenyl]-ethyl}-butan-1-ol |
| n = 2, | (S)-2-Amino-2-{2-[4-(9-methyl-octyloxy)-phenyl]-ethyl}-butan-1-ol |
| n = 3, | (S)-2-Amino-2-{2-[4-(10-methyl-nonyloxy)-phenyl]-ethyl}-butan-1-ol |
| n = 4, | (S)-2-Amino-2-{2-[4-(11-methyl-decyloxy)-phenyl]-ethyl}-butan-1-ol |
| n = 0, | (S)-2-Amino-2-{2-[4-(1,5-dimethyl-hexyloxy)-phenyl]-ethyl}-butan-1-ol |
| n = 1, | (S)-2-Amino-2-{2-[4-(2,6-dimethyl-heptyloxy)-phenyl]-ethyl}-butan-1-ol |
| n = 2, | (S)-2-Amino-2-{2-[4-(3,7-dimethyl-octyloxy)-phenyl]-ethyl}-butan-1-ol |
| n = 3, | (S)-2-Amino-2-{2-[4-(4,8-dimethyl-nonyloxy)-phenyl]-ethyl}-butan-1-ol |
| n = 4, | (S)-2-Amino-2-{2-[4-(5,9-dimethyl-decyloxy)-phenyl]-ethyl}-butan-1-ol |

Another embodiment of the invention provides the compounds of Table 2:

TABLE 2

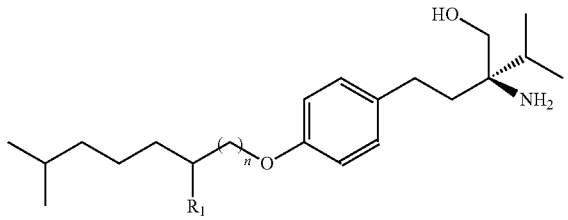

Compounds wherein $R^1$ is hydrogen or methyl, $R^2$ is hydrogen, $R^3$ is isopropyl.

| N & alkyl sidechain | Name |
|---|---|
| n = 0 | (S)-2-Amino-3-methyl-2-{2-[4-(5-methyl-hexyloxy)-phenyl]-ethyl}-butan-1-ol |
| n = 1 | (S)-2-Amino-3-methyl-2-{2-[4-(6-methyl-heptyloxy)-phenyl]-ethyl}-butan-1-ol |
| n = 2 | (S)-2-Amino-3-methyl-2-{2-[4-(7-methyl-octyloxy)-phenyl]-ethyl}-butan-1-ol |
| n = 3 | (S)-2-Amino-3-methyl-2-{2-[4-(8-methyl-nonyloxy)-phenyl]-ethyl}-butan-1-ol |
| n = 4 | (S)-2-Amino-3-methyl-2-{2-[4-(9-methyl-decyloxy)-phenyl]-ethyl}-3-methyl-butan-1-ol |
| n = 0 | (S)-2-Amino-2-{2-[4-(3,7-dimethyl-heptyloxy)-phenyl]-ethyl}-3-methyl-butan-1-ol |
| n = 1 | (S)-2-Amino-2-{2-[4-(3,7-dimethyl-heptyloxy)-phenyl]-ethyl}-3-methyl-butan-1-ol |
| n = 2 | (S)-2-Amino-2-{2-[4-(3,7-dimethyl-octyloxy)-phenyl]-ethyl}-3-methyl-butan-1-ol |
| n = 3 | (S)-2-Amino-2-{2-[4-(4,8-dimethyl-nonyloxy)-phenyl]-ethyl}-3-methyl-butan-1-ol |
| n = 4 | (S)-2-Amino-2-{2-[4-(5,9-dimethyl-decyloxy)-phenyl]-ethyl}-3-methyl-butan-1-ol |

Another embodiment of the invention provides the compounds of Table 3:

TABLE 3

Compounds wherein $R_1$ is hydrogen or methyl, $R_2$ is hydrogen, $R_3$ is isobutyl.

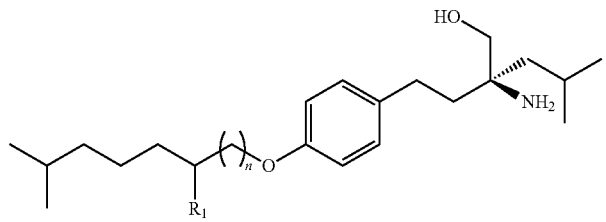

| N & alkyl sidechain | Name |
|---|---|
| n = 0, | (S)-2-Amino-4-methyl-2-{2-[4-(5-methyl-hexyloxy)-phenyl]-ethyl}-butan-1-ol |
| n = 1, | (S)-2-Amino-4-methyl-2-{2-[4-(6-methyl-heptyloxy)-phenyl]-ethyl}-butan-1-ol |
| n = 2, | (S)-2-Amino-4-methyl-2-{2-[4-(7-methyl-octyloxy)-phenyl]-ethyl}-butan-1-ol |
| n = 3, | (S)-2-Amino-4-methyl-2-{2-[4-(8-methyl-nonyloxy)-phenyl]-ethyl}-butan-1-ol |
| n = 4, | (S)-2-Amino-4-methyl-2-{2-[4-(9-methyl-decyloxy)-phenyl]-ethyl}-butan-1-ol |
| n = 0, | (S)-2-Amino-2-{2-[4-(3,7-dimethyl-hexyloxy)-phenyl]-ethyl}-4-methyl-butan-1-ol |
| n = 1, | (S)-2-Amino-2-{2-[4-(3,7-dimethyl-heptyloxy)-phenyl]-ethyl}-4-methyl-butan-1-ol |
| n = 2, | (S)-2-Amino-2-{2-[4-(3,7-dimethyl-octyloxy)-phenyl]-ethyl}-4-methyl-butan-1-ol |
| n = 3, | (S)-2-Amino-2-{2-[4-(4,8-dimethyl-nonyloxy)-phenyl]-ethyl}-4-methyl-butan-1-ol |
| n = 4, | (S)-2-Amino-2-{2-[4-(5,9-dimethyl-decyloxy)-phenyl]-ethyl}-4-methyl-butan-1-ol |

Another embodiment of the invention provides the compounds of Table 4:

TABLE 4

Compounds wherein $R^1$ is hydrogen or methyl, $R^2$ is hydrogen, $R^3$ is cyclobutylmethyl.

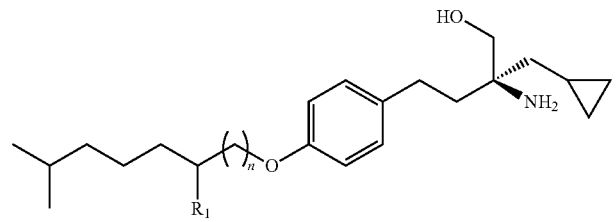

| N & alkyl sidechain | Name |
| --- | --- |
| n = 0, | (S)-2-Amino-2-cyclopropylmethyl-4-[4-(5-methyl-hexyloxy)-phenyl]-butan-1-ol |
| n = 1, | (S)-2-Amino-2-cyclopropylmethyl-4-[4-(6-methyl-heptyloxy)-phenyl]-butan-1-ol |
| n = 2, | (S)-2-Amino-2-cyclopropylmethyl-4-[4-(7-methyl-octyloxy)-phenyl]-butan-1-ol |
| n = 3, | (S)-2-Amino-2-cyclopropylmethyl-4-[4-(8-methyl-nonyloxy)-phenyl]-butan-1-ol |
| n = 4, | (S)-2-Amino-2-cyclopropylmethyl-4-[4-(9-methyl-decyloxy)-phenyl]-butan-1-ol |
| n = 0, | (S)-2-Amino-2-cyclopropylmethyl-4-[4-(1,5-dimethyl-hexyloxy)-phenyl]-butan-1-ol |
| n = 1, | (S)-2-Amino-2-cyclopropylmethyl-4-[4-(2,6-dimethyl-heptyloxy)-phenyl]-butan-1-ol |
| n = 2, | (S)-2-Amino-2-cyclopropylmethyl-4-[4-(3,7-dimethyl-octyloxy)-phenyl]-butan-1-ol |
| n = 3, | (S)-2-Amino-2-cyclopropylmethyl-4-[4-(4,8-dimethyl-nonyloxy)-pheny]-butan-1-ol |
| n = 4, | (S)-2-Amino-2-cyclopropylmethyl-4-[4-(5,9-dimethyl-decyloxy)-phenyl]-butan-1-ol |

Another embodiment of the invention provides the compounds of Table 5:

TABLE 5

Compounds wherein $R^1$ is hydrogen or methyl, $R^2$ is hydrogen, $R^3$ is cyclopropylmethyl.

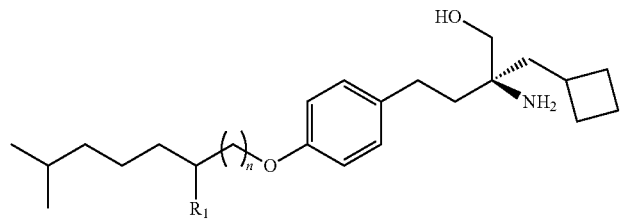

| N & alkyl sidechain | Name |
|---|---|
| n = 0, | (S)-2-Amino-2-cyclobutylmethyl-4-[4-(5-methyl-hexyloxy)-phenyl]-butan-1-ol |
| n = 1, | (S)-2-Amino-2-cyclobutylmethyl-4-[4-(6-methyl-heptyloxy)-phenyl]-butan-1-ol |
| n = 2, | (S)-2-Amino-2-cyclobutylmethyl-4-[4-(7-methyl-octyloxy)-phenyl]-butan-1-ol |
| n = 3, | (S)-2-Amino-2-cyclobutylmethyl-4-[4-(8-methyl-nonyloxy)-phenyl]-butan-1-ol |
| n = 4, | (S)-2-Amino-2-cyclobutylmethyl-4-[4-(9-methyl-decyloxy)-phenyl]-butan-1-ol |
| n = 0, | (S)-2-Amino-2-cyclobutylmethyl-4-[4-(1,5-dimethyl-hexyloxy)-phenyl]-butan-1-ol |
| n = 1, | (S)-2-Amino-2-cyclobutylmethyl-4-[4-(2,6-dimethyl-heptyloxy)-phenyl]-butan-1-ol |
| n = 2, | (S)-2-Amino-2-cyclobutylmethyl-4-[4-(3,7-dimethyl-octyloxy)-phenyl]-butan-1-ol |
| n = 3, | (S)-2-Amino-2-cyclobutylmethyl-4-[4-(4,8-dimethyl-nonyloxy)-phenyl]-butan-1-ol |
| n = 4, | (S)-2-Amino-2-cyclobutylmethyl-4-[4-(5,9-dimethyl-decyloxy)-phenyl]-butan-1-ol |

Another embodiment of the invention provides the compounds of Table 6:

TABLE 6

Compounds wherein $R^1$ is hydrogen or methyl, $R^2$ is 2-methoxy, $R^3$ is propyl.

| N & alkyl sidechain | Name |
|---|---|
| n = 0, | (S)-2-Amino-2-{2-[2-methoxy-4-(5-methyl-hexyloxy)-phenyl]-ethyl}-butan-1-ol |
| n = 1, | (S)-2-Amino-2-{2-[2-methoxy-4-(6-methyl-heptyloxy)-phenyl]-ethyl}-pentan-1-ol |
| n = 2, | (S)-2-Amino-2-{2-[2-methoxy-4-(7-methyl-octyloxy)-phenyl]-ethyl}-pentan-1-ol |
| n = 3, | (S)-2-Amino-2-{2-[2-methoxy-4-(8-methyl-nonyloxy)-phenyl]-ethyl}-butan-1-ol |
| n = 4, | (S)-2-Amino-2-{2-[2-methoxy-4-(9-methyl-decyloxy)-phenyl]-ethyl}-butan-1-ol |
| n = 0, | (S)-2-Amino-2-{2-[4-(1,5-dimethyl-hexyloxy)-2-methoxy-phenyl]-ethyl}-butan-1-ol |
| n = 1, | (S)-2-Amino-2-{2-[4-(2,6-dimethyl-heptyloxy)-2-methoxy-phenyl]-ethyl}-pentan-1-ol |
| n = 2, | (S)-2-Amino-2-{2-[4-(3,7-dimethyl-octyloxy)-2-methoxy-phenyl]-ethyl}-butan-1-ol |
| n = 3, | (S)-2-Amino-2-{2-[4-(4,8-dimethyl-nonyloxy)-2-methoxy-phenyl]-ethyl}-butan-1-ol |
| n = 4, | (S)-2-Amino-2-{2-[4-(5,9-dimethyl-decyloxy)-2-methoxy-phenyl]-ethyl}-butan-1-ol |

Another embodiment of the invention provides the compounds of Table 7:

TABLE 7

Compounds wherein $R^1$ is hydrogen or methyl, $R^2$ is 2-methoxy, $R^3$ is isopropyl.

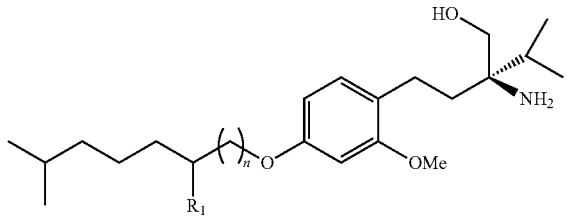

| N & alkyl sidechain | Name |
| --- | --- |
| n = 0, | (S)-2-Amino-2-{2-[2-methoxy-4-(5-methyl-hexyloxy)-phenyl]-ethyl}-3-methyl-butan-1-ol |
| n = 1, | (S)-2-Amino-2-{2-[2-methoxy-4-(6-methyl-heptyloxy)-phenyl]-ethyl}-3-methyl-butan-1-ol |
| n = 2, | (S)-2-Amino-2-{2-[2-methoxy-4-(7-methyl-octyloxy)-phenyl]-ethyl}-3-methyl-pentan-1-ol |
| n = 3, | (S)-2-Amino-2-{2-[2-methoxy-4-(8-methyl-nonyloxy)-phenyl]-ethyl}-3-methyl-butan-1-ol |
| n = 4, | (S)-2-Amino-2-{2-[2-methoxy-4-(9-methyl-decyloxy)-phenyl]-ethyl}-3-methyl-butan-1-ol |
| n = 0, | (S)-2-Amino-2-{2-[4-(1,5-dimethyl-hexyloxy)-2-methoxy-phenyl]-ethyl}-3-methyl-butan-1-ol |
| n = 1, | (S)-2-Amino-2-{2-[4-(2,6-dimethyl-heptyloxy)-2-methoxy-phenyl]-ethyl}-3-methyl-butan-1-ol |
| n = 2, | (S)-2-Amino-2-{2-[4-(3,7-dimethyl-octyloxy)-2-methoxy-phenyl]-ethyl}-3-methyl-butan-1-ol |
| n = 3, | (S)-2-Amino-2-{2-[4-(4,8-dimethyl-nonyloxy)-2-methoxy-phenyl]-ethyl}-3-methyl-butan-1-ol |
| n = 4, | (S)-2-Amino-2-{2-[4-(5,9-dimethyl-decyloxy)-2-methoxy-phenyl]-ethyl}-3-methyl-butan-1-ol |

Another embodiment of the invention provides the compounds of Table 8:

TABLE 8

Compounds wherein $R^1$ is hydrogen or methyl, $R^2$ is 2-methoxy, $R^3$ is isopropyl.

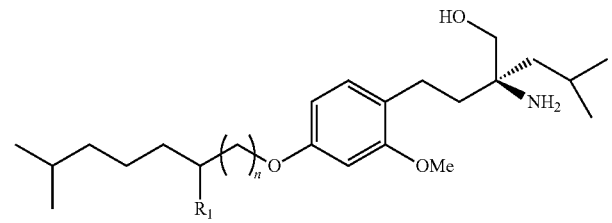

| N & alkyl sidechain | Name |
|---|---|
| n = 0, | (S)-2-Amino-2-{2-[2-methoxy-4-(5-methyl-hexyloxy)-phenyl]-ethyl}-4-methyl-pentan-1-ol |
| n = 1, | (S)-2-Amino-2-{2-[2-methoxy-4-(6-methyl-heptyloxy)-phenyl]-ethyl}-4-methyl-pentan-1-ol |
| n = 2, | (S)-2-Amino-2-{2-[2-methoxy-4-(7-methyl-octyloxy)-phenyl]ethyl}-4-methyl-pentan-1-ol |
| n = 3, | (S)-2-Amino-2-{2-[2-methoxy-4-(8-methyl-nonyloxy)-phenyl]-ethyl}-4-methyl-pentan-1-ol |
| n = 4, | (S)-2-Amino-2-{2-[2-methoxy-4-(9-methyl-decyloxy)-phenyl]-ethyl}-4-methyl-pentan-1-ol |
| n = 0, | (S)-2-Amino-2-{2-[4-(1,5-dimethyl-hexyloxy)-2-methoxy-phenyl]-ethyl}-4-methyl-pentan-1-ol |
| n = 1, | (S)-2-Amino-2-{2-[4-(2,6-dimethyl-heptyloxy)-2-methoxy-phenyl]-ethyl}-4-methyl-pentan-1-ol |
| n = 2, | (S)-2-Amino-2-{2-[4-(3,7-dimethyl-octyloxy)-2-methoxy-phenyl]-ethyl}-4-methyl-pentan-1-ol |
| n = 3, | (S)-2-Amino-2-{2-[4-(4,8-dimethyl-nonyloxy)-2-methoxy-phenyl]-ethyl}-4-methyl-pentan-1-ol |
| n = 4, | (S)-2-Amino-2-{2-[4-(5,9-dimethyl-decyloxy)-2-methoxy-phenyl]-ethyl}-4-methyl-pentan-1-ol |

Another embodiment of the invention provides the compounds of Table 9:

TABLE 9

Compounds wherein R¹ is hydrogen or methyl, R² is 2-methoxy, R³ is cyclopropylmethyl.

| N & alkyl sidechain | Name |
|---|---|
| n = 0, | (S)-2-Amino-2-cyclopropylmethyl-4-[4-(5-methyl-hexyloxy)-2-methoxy-phenyl]-butan-1-ol |
| n = 1, | (S)-2-Amino-2-cyclopropylmethyl-4-[4-(6-methyl-heptyloxy)-2-methoxy-phenyl]-butan-1-ol |
| n = 2, | (S)-2-Amino-2-cyclopropylmethyl-4-[4-(7-methyl-octyloxy)-2-methoxy-phenyl]-butan-1-ol |
| n = 3, | (S)-2-Amino-2-cyclopropylmethyl-4-[4-(8-methyl-nonyloxy)-2-methoxy-phenyl]-butan-1-ol |
| n = 4, | (S)-2-Amino-2-cyclopropylmethyl-4-[4-(9-methyl-decyloxy)-2-methoxy-phenyl]-butan-1-ol |
| n = 0, | (S)-2-Amino-2-cyclopropylmethyl-4-[4-(1,5-dimethyl-hexyloxy)-2-methoxy-phenyl]-butan-1-ol |
| n = 1, | (S)-2-Amino-2-cyclopropylmethyl-4-[4-(2,6-dimethyl-heptyloxy)-2-methoxy-phenyl]-butan-1-ol |
| n = 2, | (S)-2-Amino-2-cyclopropylmethyl-4-[4-(3,7-dimethyl-octyloxy)-2-methoxy-phenyl]-butan-1-ol |
| n = 3, | (S)-2-Amino-2-cyclopropylmethyl-4-[4-(4,8-dimethyl-nonyloxy)-2-methoxy-phenyl]-butan-1-ol |
| n = 4, | (S)-2-Amino-2-cyclopropylmethyl-4-[4-(5,9-dimethyl-decyloxy)-2-methoxy-phenyl]-butan-1-ol |

Another embodiment of the invention provides the compounds of Table 10:

TABLE 10

Compounds wherein $R^1$ is hydrogen or methyl, $R^2$ is 2-methoxy, $R^3$ is cyclopropylmethyl.

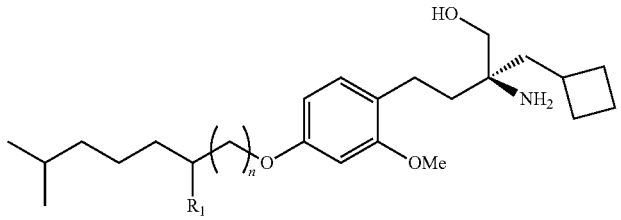

| N & alkyl sidechain | Name |
|---|---|
| n = 0, | (S)-2-Amino-2-cyclobutylmethyl-4-[4-(5-methyl-hexyloxy)-2-methoxy-phenyl]-butan-1-ol |
| n = 1, | (S)-2-Amino-2-cyclobutylmethyl-4-[4-(6-methyl-heptyloxy)-2-methoxy-phenyl]-butan-1-ol |
| n = 2, | (S)-2-Amino-2-cyclobutylmethyl-4-[4-(7-methyl-octyloxy)-2-methoxy-phenyl]-butan-1-ol |
| n = 3, | (S)-2-Amino-2-cyclobutylmethyl-4-[4-(8-methyl-nonyloxy)-2-methoxy-phenyl]-butan-1-ol |
| n = 4, | (S)-2-Amino-2-cyclobutylmethyl-4-[4-(9-methyl-decyloxy)-phenyl]-2-methoxy-butan-1-ol |
| n = 0, | (S)-2-Amino-2-cyclobutylmethyl-4-[4-(1,5-dimethyl-hexyloxy)-2-methoxy-phenyl]-butan-1-ol |
| n = 1, | (S)-2-Amino-2-cyclobutylmethyl-4-[4-(2,6-dimethyl-heptyloxy)-2-methoxy-phenyl]-butan-1-ol |
| n = 2, | (S)-2-Amino-2-cyclobutylmethyl-4-[4-(3,7-dimethyl-octyloxy)-2-methoxy-phenyl]-butan-1-ol |
| n = 3, | (S)-2-Amino-2-cyclobutylmethyl-4-[4-(4,8-dimethyl-nonyloxy)-2-mehtoxy-phenyl]-butan-1-ol |
| n = 4, | (S)-2-Amino-2-cyclobutylmethyl-4-[4-(5,9-dimethyl-decyloxy)-2-methoxy-phenyl]-butan-1-ol |

Another embodiment of the invention provides the compounds of Table 11:

TABLE 11

Compounds wherein $R^1$ is hydrogen or methyl, $R^2$ is 2-hydroxy, $R^3$ is propyl.

| N & alkyl sidechain | Name |
|---|---|
| n = 0, | (S)-2-Amino-2-{2-[2-hydroxy-4-(5-methyl-hexyloxy)-phenyl]-ethyl}-butan-1-ol |
| n = 1, | (S)-2-Amino-2-{2-[2-hydroxy-4-(6-methyl-heptyloxy)-phenyl]-ethyl}-pentan-1-ol |
| n = 2, | (S)-2-Amino-2-{2-[2-hydroxy-4-(7-methyl-octyloxy)-phenyl]-ethyl}-pentan-1-ol |
| n = 3, | (S)-2-Amino-2-{2-[2-hydroxy-4-(8-methyl-nonyloxy)-phenyl]-ethyl}-butan-1-ol |
| n = 4, | (S)-2-Amino-2-{2-[2-hydroxy-4-(9-methyl-decyloxy)-phenyl]-ethyl}-butan-1-ol |
| n = 0, | (S)-2-Amino-2-{2-[4-(1,5-dimethyl-hexyloxy)-2-hydroxy-pheny]-ethyl}-butan-1-ol |
| n = 1, | (S)-2-Amino-2-{2-[4-(2,6-dimethyl-heptyloxy)-2-hydroxy-phenyl]-ethyl}-pentan-1-ol |
| n = 2, | (S)-2-Amino-2-{2-[4-(3,7-dimethyl-octyloxy)-2-hydroxy-phenyl]-ethyl}-butan-1-ol |
| n = 3, | (S)-2-Amino-2-{2-[4-(4,8-dimethyl-nonyloxy)-2-hydroxy-phenyl]-ethyl}-butan-1-ol |
| n = 4, | (S)-2-Amino-2-{2-[4-(5,9-dimethyl-decyloxy)-2-hydroxy-phenyl]-ethyl}-butan-1-ol |

Another embodiment of the invention provides the compounds of Table 12:

TABLE 12

Compounds wherein $R^1$ is hydrogen or methyl, $R^2$ is 2-hydroxy, $R^3$ is isopropyl.

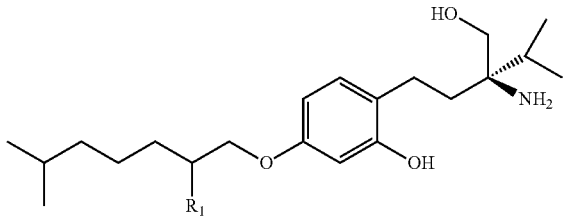

| N & alkyl sidechain | Name |
|---|---|
| n = 0, | (S)-2-Amino-2-{2-[2-hydroxy-4-(5-methyl-hexyloxy)-phenyl]-ethyl}-4-methyl-pentan-1-ol |
| n = 1, | (S)-2-Amino-2-{2-[2-hydroxy-4-(6-methyl-heptyloxy)-phenyl]-ethyl}-4-methyl-pentan-1-ol |
| n = 2, | (S)-2-Amino-2-{2-[2-hydroxy-4-(7-methyl-octyloxy)-phenyl]-ethyl}-4-methyl-pentan-1-ol |
| n = 3, | (S)-2-Amino-2-{2-[2-hydroxy-4-(8-methyl-nonyloxy)-phenyl]-ethyl}-4-methyl-pentan-1-ol |
| n = 4, | (S)-2-Amino-2-{2-[2-hydroxy-4-(9-methyl-decyloxy)-phenyl]-ethyl}-4-methyl-pentan-1-ol |
| n = 0, | (S)-2-Amino-2-{2-[4-(1,5-dimethyl-hexyloxy)-2-hydrooxy-phenyl]-ethyl}-4-methyl-pentan-1-ol |
| n = 1, | (S)-2-Amino-2-{2-[4-(2,6-dimethyl-heptyloxy)-2-hydroxy-phenyl]-ethyl}-4 ethyl-pentan-1-ol |
| n = 2, | (S)-2-Amino-2-{2-[4-(3,7-dimethyl-octyloxy)-2-hydroxy-phenyl]-ethyl}-4-methyl-pentan-1-ol |
| n = 3, | (S)-2-Amino-2-{2-[4-(4,8-dimethyl-nonyloxy)-2-hydroxy-phenyl]-ethyl}-4-methyl-pentan-1-ol |
| n = 4, | (S)-2-Amino-2-{2-[4-(5,9-dimethyl-decyloxy)-2-hydroxy-phenyl]-ethyl}-4-methyl-pentan-1-ol |

Another embodiment of the invention provides the compounds of Table 13:

TABLE 13

Compounds wherein $R^1$ is hydrogen or methyl, $R^2$ is 2-hydroxy, $R^3$ is isobutyl.

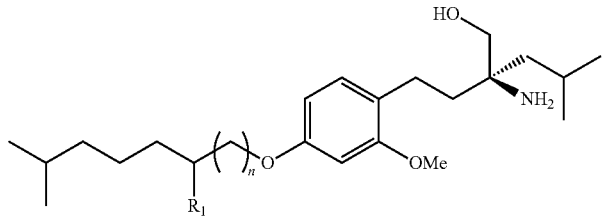

| N & alkyl sidechain | Name |
| --- | --- |
| n = 0 | (S)-2-Amino-2-{2-[2-hydroxy-4-(5-methyl-hexyloxy)-phenyl]-ethyl}-4-methyl-pentan-1-ol |
| n = 1 | (S)-2-Amino-2-{2-[2-hydroxy-4-(6-methyl-heptyloxy)-phenyl]-ethyl}-4-methyl-pentan-1-ol |
| n = 2 | (S)-2-Amino-2-{2-[2-hydroxy-4-(7-methyl-octyloxy)-phenyl]-ethyl}-4-methyl-pentan-1-ol |
| n = 3 | (S)-2-Amino-2-{2-[2-hydroxy-4-(8-methyl-nonyloxy)-phenyl]-ethyl}-4-methyl-pentan-1-ol |
| n = 4 | (S)-2-Amino-2-{2-[2-hydroxy-4-(9-methyl-decyloxy)-phenyl]-ethyl}-4-methyl-pentan-1-ol |
| n = 0 | (S)-2-Amino-2-{2-[4-(1,5-dimethyl-hexyloxy)-2-hydroxy-phenyl]-ethyl}-4-methyl-pentan-1-ol |
| n = 1 | (S)-2-Amino-2-{2-[4-(2,6-dimethyl-heptyloxy)-2-hydroxy-phenyl]-ethyl}-4-methyl-pentan-1-ol |
| n = 2 | (S)-2-Amino-2-{2-[4-(3,7-dimethyl-octyloxy)-2-hydroxy-phenyl]-ethyl}-4-methyl-pentan-1-ol |
| n = 3 | (S)-2-Amino-2-{2-[4-(4,8-dimethyl-nonyloxy)-2-hydroxy-phenyl]-ethyl}-4-methyl-pentan-1-ol |
| n = 4 | (S)-2-Amino-2-{2-[4-(5,9-dimethyl-decyloxy)-2-hydroxy-phenyl]-ethyl}-4-methyl-pentan-1-ol |

Another embodiment of the invention provides the compounds of Table 14:

TABLE 14

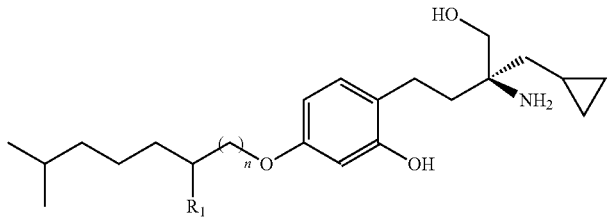

Compounds wherein $R^1$ is hydrogen or methyl, $R^2$ is 2-hydroxy, $R^3$ is cyclopropylmethyl.

| N & alkyl sidechain | Name |
|---|---|
| n = 0, | (S)-2-Amino-2-cyclopropylmethyl-4-[4-(5-methyl-hexyloxy)-2-hydroxy-phenyl]-butan-1-ol |
| n = 1, | (S)-2-Amino-2-cyclopropylmethyl-4-[4-(6-methyl-heptyloxy)-2-hydroxy-phenyl]-butan-1-ol |
| n = 2, | (S)-2-Amino-2-cyclopropylmethyl-4-[4-(7-methyl-octyloxy)-2-hydroxy-phenyl]-butan-1-ol |
| n = 3, | (S)-2-Amino-2-cyclopropylmethyl-4-[4-(8-methyl-nonyloxy)-2-hydroxy-phenyl]-butan-1-ol |
| n = 4, | (S)-2-Amino-2-cyclopropylmethyl-4-[4-(9-methyl-decyloxy)-2-hydroxy-phenyl]-butan-1-ol |
| n = 0, | (S)-2-Amino-2-cyclopropylmethyl-4-[4-(1,5-dimethyl-hexyloxy)-2-hydroxy-phenyl]-butan-1-ol |
| n = 1, | (S)-2-Amino-2-cyclopropylmethyl-4-[4-(2,6-dimethyl-heptyloxy)-2-hydroxy-phenyl]-butan-1-ol |
| n = 2, | (S)-2-Amino-2-cyclopropylmethyl-4-[4-(3,7-dimethyl-octyloxy)-2-hydroxy-phenyl]-butan-1-ol |
| n = 3, | (S)-2-Amino-2-cyclopropylmethyl-4-[4-(4,8-dimethyl-nonyloxy)-2-hydroxy-phenyl]-butan-1-ol |
| n = 4, | (S)-2-Amino-2-cyclopropylmethyl-4-[4-(5,9-dimethyl-decyloxy)-2-hydroxy-phenyl]-butan-1-ol |

Another embodiment of the invention provides the compounds of Table 15:

TABLE 15

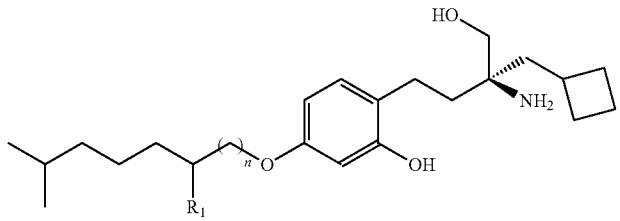

Compounds wherein $R^1$ is hydrogen or methyl, $R^2$ is 2-hydroxy, $R^3$ is cyclobutylmethyl.

| N & alkyl sidechain | Name |
|---|---|
| n = 0, | (S)-2-Amino-2-cyclobutylmethyl-4-[4-(5-methyl-hexyloxy)-2-hydroxy-phenyl]-butan-1-ol |
| n = 1, | (S)-2-Amino-2-cyclobutylmethyl-4-[4-(6-methyl-heptyloxy)-2-hydroxy-phenyl]-butan-1-ol |
| n = 2, | (S)-2-Amino-2-cyclobutylmethyl-4-[4-(7-methyl-octyloxy)-2-hydroxy-phenyl]-butan-1-ol |
| n = 3, | (S)-2-Amino-2-cyclobutylmethyl-4-[4-(8-methyl-nonyloxy)-2-hydroxy-phenyl]-butan-1-ol |
| n = 4, | (S)-2-Amino-2-cyclobutylmethyl-4-[4-(9-methyl-decyloxy)-phenyl]-2-hydroxy-butan-1-ol |
| n = 0, | (S)-2-Amino-2-cyclobutylmethyl-4-[4-(1,5-dimethyl-hexyloxy)-2-hydroxy-phenyl]-butan-1-ol |
| n = 1, | (S)-2-Amino-2-cyclobutylmethyl-4-[4-(2,6-dimethyl-heptyloxy)-2-hydroxy-phenyl]-butan-1-ol |
| n = 2, | (S)-2-Amino-2-cyclobutylrnethyl-4-[4-(3,7-dimethyl-octyloxy)-2-hydroxy-phenyl]-butan-1-ol |
| n = 3, | (S)-2-Amino-2-cyclobutylmethyl-4-[4-(4,8-dimethyl-nonyloxy)-2-hydroxy-phenyl]-butan-1-ol |
| n = 4, | (S)-2-Amino-2-cyclobutylmethyl-4-[4-(5,9-dimethyl-decyloxy)-2-hydroxy-phenyl]-butan-1-ol |

Another embodiment of the invention provides the compounds of Table 16:

TABLE 16

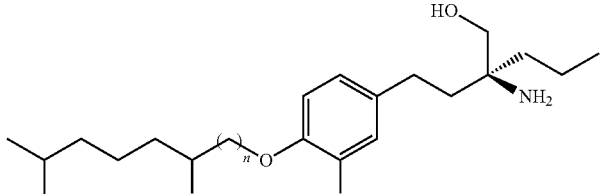

Compounds wherein $R^1$ is hydrogen or methyl, $R^2$ is 3-methoxy, $R^3$ is propyl.

| N & alkyl sidechain | | Name |
|---|---|---|
| n = 0, | 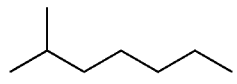 | (S)-2-Amino-2-{2-[3-methoxy-4-(5-methyl-hexyloxy)-phenyl]-ethyl}-butan-1-ol |
| n = 1, | 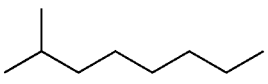 | (S)-2-Amino-2-{2-[3-methoxy-4-(6-methyl-heptyloxy)-phenyl]-ethyl}-pentan-1-ol |
| n = 2, | 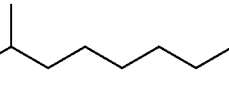 | (S)-2-Amino-2-{2-[3-methoxy-4-(7-methyl-octyloxy)-phenyl]-ethyl}-pentan-1-ol |
| n = 3, | 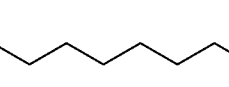 | (S)-2-Amino-2-{2-[3-methoxy-4-(8-methyl-nonyloxy)-phenyl]-ethyl}-butan-1-ol |
| n = 4, | 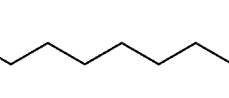 | (S)-2-Amino-2-{2-[3-methoxy-4-(9-methyl-decyloxy)-phenyl]-ethyl}-butan-1-ol |
| n = 0, | 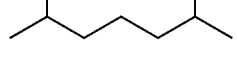 | (S)-2-Amino-2-{2-[4-(1,5-dimethyl-hexyloxy)-3-methoxy-phenyl]-ethyl}-butan-1-ol |
| n = 1, | 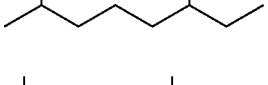 | (S)-2-Amino-2-{2-[4-(2,6-dimethyl-heptyloxy)-3-methoxy-phenyl]-ethyl}-pentan-1-ol |
| n = 2, | 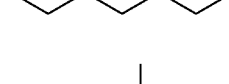 | (S)-2-Amino-2-{2-[4-(3,7-dimethyl-octyloxy)-3-methoxy-phenyl]ethyl}-butan-1-ol |
| n = 3, |  | (S)-2-Amino-2-{2-[4-(4,8-dimethyl-nonyloxy)-3-methoxy-phenyl]-ethyl}-butan-1-ol |
| n = 4, | 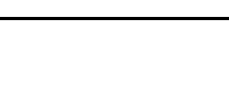 | (S)-2-Amino-2-{2-[4-(5,9-dimethyl-decyloxy)-3-methoxy-phenyl]-ethyl}-butan-1-ol |

Another embodiment of the invention provides the compounds of Table 17:

TABLE 17

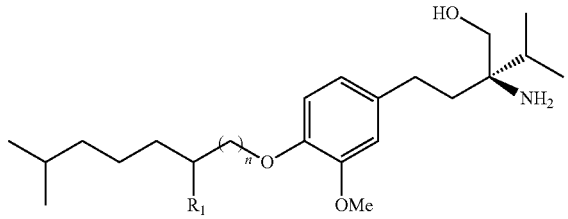

Compounds wherein $R^1$ is hydrogen or methyl, $R^2$ is 3-methoxy, $R^3$ is isopropyl.

| N & alkyl sidechain | Name |
|---|---|
| n = 0 | (S)-2-Amino-2-{2-[3-methoxy-4-(5-methyl-hexyloxy)-phenyl]-ethyl}-3-methyl-butan-1-ol |
| n = 1 | (S)-2-Amino-2-{2-[3-methoxy-4-(6-methyl-heptyloxy)-phenyl]-ethyl}-3-methyl-butan-1-ol |
| n = 2 | (S)-2-Amino-2-{2-[3-methoxy-4-(7-methyl-octyloxy)-phenyl]-ethyl}-3-methyl-pentan-1-ol |
| n = 3 | (S)-2-Amino-2-{2-[3-methoxy-4-(8-methyl-nonyloxy)-phenyl]-ethyl}-3-methyl-butan-1-ol |
| n = 4 | (S)-2-Amino-2-{2-[3-methoxy-4-(9-methyl-decyloxy)-phenyl]-ethyl}-3-methyl-butan-1-ol |
| n = 0 | (S)-2-Amino-2-{2-[4-(1,5-dimethyl-hexyloxy)-3-methoxy-phenyl]ethyl}-3-methyl-butan-1-ol |
| n = 1 | (S)-2-Amino-2-{2-[4-(2,6-dimethyl-heptyloxy)-3-methoxy-phenyl]-ethyl}-3-methyl-butan-1-ol |
| n = 2 | (S)-2-Amino-2-{2-[4-(3,7-dimethyl-octyloxy)-3-methoxy-phenyl]-ethyl}-3-methyl-butan-1-ol |
| n = 3 | (S)-2-Amino-2-{2-[4-(4,8-dimethyl-nonyloxy)-3-methoxy-phenyl]-ethyl}-3-methyl-butan-1-ol |
| n = 4 | (S)-2-Amino-2-{2-[4-(5,9-dimethyl-decyloxy)-3-methoxy-phenyl]-ethyl}-3-methyl-butan-1-ol |

Another embodiment of the invention provides the compounds of Table 18:

TABLE 18

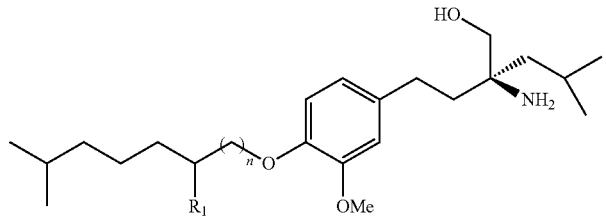

Compounds wherein $R^1$ is hydrogen or methyl, $R^2$ is 3-methoxy, $R^3$ is isobutyl.

| N & alkyl sidechain | Name |
|---|---|
| n = 0, | (S)-2-Amino-2-{2-[3-methoxy-4-(5-methyl-hexyloxy)-phenyl]-ethyl}-4-methyl-pentan-1-ol |
| n = 1, | (S)-2-Amino-2-{2-[3-methoxy-4-(6-methyl-heptyloxy)-phenyl]-ethyl}-4-methyl-pentan-1-ol |
| n = 2, | (S)-2-Amino-2-{2-[3-methoxy-4-(7-methyl-octyloxy)-phenyl]-ethyl}-4-methyl-pentan-1-ol |
| n = 3, | (S)-2-Amino-2-{2-[3-methoxy-4-(8-methyl-nonyloxy)-phenyl]-ethyl}-4-methyl-pentan-1-ol |
| n = 4, | (S)-2-Amino-2-{2-[3-methoxy-4-(9-methyl-decyloxy)-phenyl]-ethyl}-4-methyl-pentan-1-ol |
| n = 0, | (S)-2-Amino-2-{2-[4-(1,5-dimethyl-hexyloxy)-3-methoxy-phenyl]-ethyl}-4-methyl-pentan-1-ol |
| n = 1, | (S)-2-Amino-2-{2-[4-(2,6-dimethyl-heptyloxy)-3-methoxy-phenyl]-ethyl}-4-methyl-pentan-1-ol |
| n = 2, | (S)-2-Amino-2-{2-[4-(3,7-dimethyl-octyloxy)-3-methoxy-phenyl]-ethyl}-4-methyl-pentan-1-ol |
| n = 3, | (S)-2-Amino-2-{2-[4-(4,8-dimethyl-nonyloxy)-3-methoxy-phenyl]-ethyl}-4-methyl-pentan-1-ol |
| n = 4, | (S)-2-Amino-2-{2-[4-(5,9-dimethyl-decyloxy)-3-methoxy-phenyl]-ethyl}-4-methyl-pentan-1-ol |

Another embodiment of the invention provides the compounds of Table 19:

TABLE 19

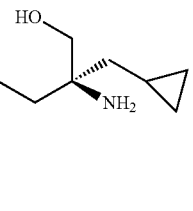

Compounds wherein R¹ is hydrogen or methyl, R² is 3-methoxy, R³ is cyclopropylmethyl

| N & alkyl sidechain | | Name |
|---|---|---|
| n = 0, | 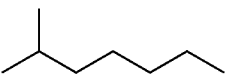 | (S)-2-Amino-2-cyclopropylmethyl-4-[4-(5-methyl-hexyloxy)-3-methoxy-phenyl]-butan-1-ol |
| n = 1, | 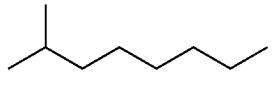 | (S)-2-Amino-2-cyclopropylrnethyl-4-[4-(6-methyl-heptyloxy)-3-methoxy-phenyl]-butan-1-ol |
| n = 2, | 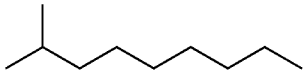 | (S)-2-Amino-2-cyclopropylmethyl-4-[4-(7-methyl-octyloxy)-3-methoxy-phenyl]-butan-1-ol |
| n = 3, | 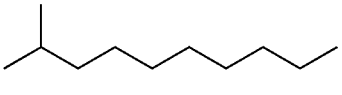 | (S)-2-Amino-2-cyclopropylmethyl-4-[4-(8-methyl-nonyloxy)-3-methoxy-phenyl]-butan-1-ol |
| n = 4, | 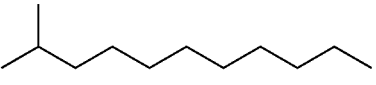 | (S)-2-Amino-2-cyclopropylmethyl-4-[4-(9-methyl-decyloxy)-3-methoxy-phenyl]-butan-1-ol |
| n = 0, | 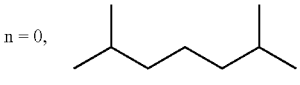 | (S)-2-Amino-2-cyclopropylmethyl-4-[4-(1,5-dimethyl-hexyloxy)-3-methoxy-phenyl]-butan-1-ol |
| n = 1, | 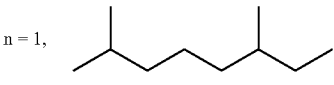 | (S)-2-Amino-2-cyclopropylmethyl-4-[4-(2,6-dimethyl-heptyloxy)-3-methoxy-phenyl]-butan-1-ol |
| n = 2, | 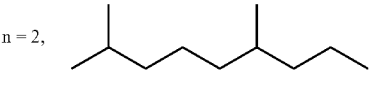 | (S)-2-Amino-2-cyclopropylmethyl-4-[4-(3,7-dimethyl-octyloxy)-3-methoxy-phenyl]-butan-1-ol |
| n = 3, | 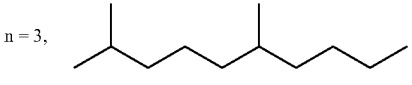 | (S)-2-Amino-2-cyclopropylmethyl-4-[4-(4,8-dimethyl-nonyloxy)-3-methoxy-phenyl]-butan-1-ol |
| n = 4, | 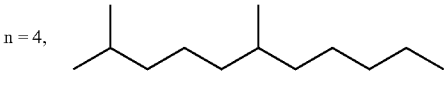 | (S)-2-Amino-2-cyclopropylmethyl-4-[4-(5,9-dimethyl-decyloxy)-3-methoxy-phenyl]-butan-1-ol |

Another embodiment of the invention provides the compounds of Table 20:

TABLE 20

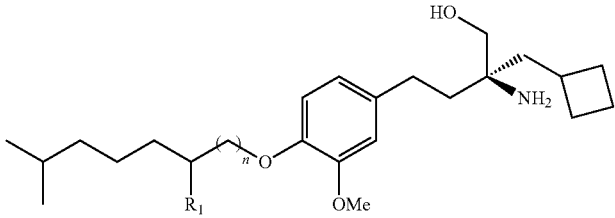

Compounds wherein $R^1$ is hydrogen or methyl, $R^2$ is 3-methoxy, $R^3$ is cyclobutylmethyl.

| N & alkyl sidechain | Name |
|---|---|
| n = 0, | (S)-2-Amino-2-cyclobutylmethyl-4-[4-(5-methyl-hexyloxy)-3-methoxy-phenyl]-butan-1-ol |
| n = 1, | (S)-2-Amino-2-cyclobutylmethyl-4-[4-(6-methyl-heptyloxy)-3-mehtoxy-phenyl]-butan-1-ol |
| n = 2, | (S)-2-Arnino-2-cyclobutyhnethyl-4-[4-(7-methyl-octyloxy)-3-methoxy-phenyl]-butan-1-ol |
| n = 3, | (S)-2-Amino-2-cyclobutylmethyl-4-[4-(8-methyl-nonyloxy)-3-methoxy-phenyl]-butan-1-ol |
| n = 4, | (S)-2-Amino-2-cyclobutylmethyl-4-[4-(9-methyl-decyloxy)-phenyl]-3-methoxy-butan-1-ol |
| n = 0, | (S)-2-Amino-2-cyclobutylmethyl-4-[4-(1,5-dimethyl-hexyloxy)-3-methoxy-phenyl]-butan-1-ol |
| n = 1, | (S)-2-Amino-2-cyclobutylmethyl-4-[4-(2,6-dimethyl-heptyloxy)-3-methoxy-phenyl]-butan-1-ol |
| n = 2, | (S)-2-Amino-2-cyclobutylmethyl-4-[4-(3,7-dimethyl-octyloxy)-3-rnethoxy-phenyl]-butan-1-ol |
| n = 3, | (S)-2-Amino-2-cyclobutylmethyl-4-[4-(4,8-dimethyl-nonyloxy)-3-mehtoxy-phenyl]-butan-1-ol |
| n = 4, | (S)-2-Amino-2-cyclobutylmethyl-4-[4-(5,9-dimethyl-decyloxy)-3-methoxy-phenyl]-butan-1-ol |

Another embodiment of the invention provides the compounds of Table 21:

TABLE 21

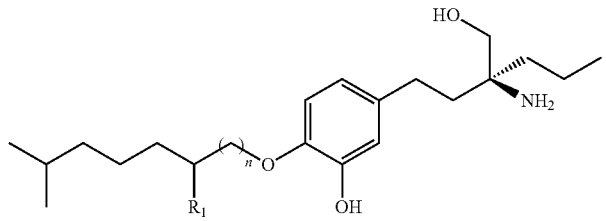

Compounds wherein $R^1$ is hydrogen or methyl, $R^2$ is 3-hydroxy, $R^3$ is propyl.

| N & alkyl sidechain | | Name |
|---|---|---|
| n = 0, | | (S)-2-Amino-2-{2-[3-hydroxy-4-(5-methyl-hexyloxy)-phenyl]-ethyl}-butan-1-ol |
| n = 1, | | (S)-2-Amino-2-{2-[3-hydroxy-4-(6-methyl-heptyloxy)-phenyl]-ethyl}-pentan-1-ol |
| n = 2, | | (S)-2-Amino-2-{2-[3-hydroxy-4-(7-methyl-octyloxy)-phenyl]-ethyl}-pentan-1-ol |
| n = 3, | | (S)-2-Amino-2-{2-[3-hydroxy-4-(8-methyl-nonyloxy)-phenyl]-ethyl}-butan-1-ol |
| n = 4, | | (S)-2-Amino-2-{2-[3-hydroxy-4-(9-methyl-decyloxy)-phenyl]-ethyl}-butan-1-ol |
| n = 0, | | (S)-2-Amino-2-{2-[4-(1,5-dimethyl-hexyloxy)-3-hydroxy-phenyl]-ethyl}-butan-1-ol |
| n = 1, | | (S)-2-Amino-2-{2-[4-(2,6-dimethyl-heptyloxy)-3-hydroxy-phenyl]-ethyl}-pentan-1-ol |
| n = 2, | | (S)-2-Amino-2-{2-[4-(3,7-dimethyl-octyloxy)-3-hydroxy-phenyl]-ethyl}-butan-1-ol |
| n = 3, | | (S)-2-Amino-2-{2-[4-(4,8-dimethyl-nonyloxy)-3-hydroxy-phenyl]-ethyl}-butan-1-ol |
| n = 4, | | (S)-2-Amino-2-{2-[4-(5,9-dimethyl-decyloxy)-3-hydroxy-phenyl]-ethyl}-butan-1-ol |

Another embodiment of the invention provides the compounds of Table 22:

TABLE 22

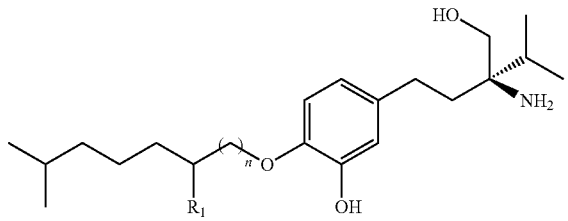

Compounds wherein $R^1$ is hydrogen or methyl, $R^2$ is 3-hydroxy, $R^3$ is isopropyl.

| N & alkyl sidechain | Name |
| --- | --- |
| n = 0 | (S)-2-Amino-2-{2-[3-hydroxy-4-(5-methyl-hexyloxy)-phenyl]-ethyl}-4-methyl-pentan-1-ol |
| n = 1 | (S)-2-Amino-2-{2-[3-hydroxy-4-(6-methyl-heptyloxy)-phenyl]-ethyl}-4-methyl-pentan-1-ol |
| n = 2 | (S)-2-Amino-2-{2-[3-hydroxy-4-(7-methyl-octyloxy)-phenyl]-ethyl}-4-methyl-pentan-1-ol |
| n = 3 | (S)-2-Amino-2-{2-[3-hydroxy-4-(8-methyl-nonyloxy)-phenyl]-ethyl}-4-methyl-pentan-1-ol |
| n = 4 | (S)-2-Amino-2-{2-[3-hydroxy-4-(9-methyl-decyloxy)-phenyl]-ethyl}-4-methyl-pentan-1-ol |
| n = 0 | (S)-2-Amino-2-{2-[4-(1,5-dimethyl-hexyloxy)-3-hydrooxy-phenyl]-ethyl}-4-methyl-pentan-1-ol |
| n = 1 | (S)-2-Amino-2-{2-[4-(2,6-dimethyl-heptyloxy)-3-hydroxy-phenyl]-ethyl}-4-methyl-pentan-1-ol |
| n = 2 | (S)-2-Amino-2-{2-[4-(3,7-dimethyl-octyloxy)-3-hydroxy-phenyl]-ethyl}-4-methyl-pentan-1-ol |
| n = 3 | (S)-2-Amino-2-{2-[4-(4,8-dimethyl-nonyloxy)-3-hydroxy-phenyl]-ethyl}-4-methyl-pentan-1-ol |
| n = 4 | (S)-2-Amino-2-{2-[4-(5,9-dimethyl-decyloxy)-3-hydroxy-phenyl]-ethyl}-4-methyl-pentan-1-ol |

Another embodiment of the invention provides the compounds of Table 23:

TABLE 23

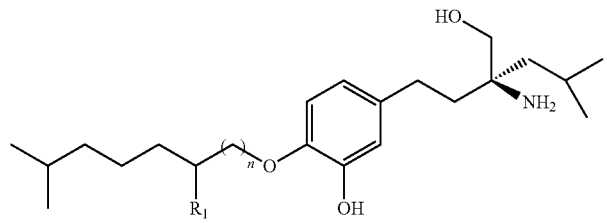

Compounds wherein $R^1$ is hydrogen or methyl, $R^2$ is 3-hydroxy, $R^3$ is isobutyl.

| N & alkyl sidechain | Name |
| --- | --- |
| n = 0, | (S)-2-Amino-2-{2-[3-hydroxy-4-(5-methyl-hexyloxy)-phenyl]-ethyl}-4-methyl-pentan-1-ol |
| n = 1, | (S)-2-Amino-2-{2-[3-hydroxy-4-(6-methyl-heptyloxy)-phenyl]-ethyl}-4-methyl-pentan-1-ol |
| n = 2, | (S)-2-Amino-2-{2-[3-hydroxy-4-(7-methyl-octyloxy)-phenyl]-ethyl}-4-methyl-pentan-1-ol |
| n = 3, | (S)-2-Amino-2-{2-[3-hydroxy-4-(8-methyl-nonyloxy)-phenyl]-ethyl}-4-methyl-pentan-1-ol |
| n = 4, | (S)-2-Amino-2-{2-[3-hydroxy-4-(9-methyl-decyloxy)-phenyl]-ethyl}-4-methyl-pentan-1-ol |
| n = 0, | (S)-2-Amino-2-{2-[4-(1,5-dimethyl-hexyloxy)-3-hydroxy-phenyl]-ethyl}-4-methyl-pentan-1-ol |
| n = 1, | (S)-2-Amino-2-{2-[4-(2,6-dimethyl-heptyloxy)-3-hydroxy-phenyl]-ethyl}-4-methyl-pentan-1-ol |
| n = 2, | (S)-2-Amino-2-{2-[4-(3,7-dimethyl-octyloxy)-3-hydroxy-phenyl]-ethyl}-4-methyl-pentan-1-ol |
| n = 3, | (S)-2-Amino-2-{2-[4-(4,8-dimethyl-nonyloxy)-3-hydroxy-phenyl]-ethyl}-4-methyl-pentan-1-ol |
| n = 4, | (S)-2-Amino-2-{2-[4-(5,9-dimethyl-decyloxy)-3-hydroxy-phenyl]-ethyl}-4-methyl-pentan-1-ol |

The compound of claim 1, And their (R)-enantiomers,

TABLE 24

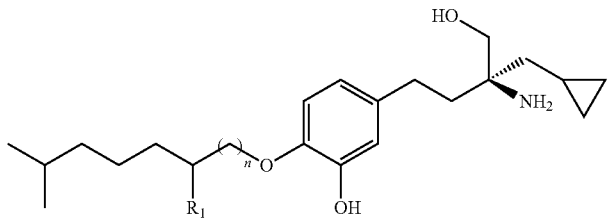

Compounds wherein $R^1$ is hydrogen or methyl, $R^2$ is 3-hydroxy, $R^3$ is cyclopropylmethyl.

| N & alkyl sidechain | Name |
|---|---|
| n = 0 | (S)-2-Amino-2-cyclopropylmethyl-4-[4-(5-methyl-hexyloxy)-3-hydroxy-phenyl]-butan-1-ol |
| n = 1 | (S)-2-Amino-2-cyclopropylrnethyl-4-[4-(6-methyl-heptyloxy)-3-hydroxy-phenyl]-butan-1-ol |
| n = 2 | (S)-2-Amino-2-cyclopropylmethyl-4-[4-(7-methyl-octyloxy)-3-hydroxy-phenyl]-butan-1-ol |
| n = 3 | (S)-2-Amino-2-cyclopropylmethyl-4-[4-(8-methyl-nonyloxy)-3-hydroxy-phenyl]-butan-1-ol |
| n = 4 | (S)-2-Amino-2-cyclopropylmethyl-4-[4-(9-methyl-decyloxy)-3-hydroxy-phenyl]-butan-1-ol |
| n = 0 | (S)-2-Amino-2-cyclopropylmethyl-4-[4-(1,5-dimethyl-hexyloxy)-3-hydroxy-phenyl]-butan-1-ol |
| n = 1 | (S)-2-Amino-2-cyclopropylmethyl-4-[4-(2,6-dimethyl-heptyloxy)-3-hydroxy-phenyl]-butan-1-ol |
| n = 2 | (S)-2-Amino-2-cyclopropylmethyl-4-[4-(3,7-dimethyl-octyloxy)-3-hydroxy-phenyl]-butan-1-ol |
| n = 3 | (S)-2-Amino-2-cyclopropylmethyl-4-[4-(4,8-dimethyl-nonyloxy)-3-hydroxy-phenyl]-butan-1-ol |
| n = 4 | (S)-2-Amino-2-cyclopropylmethyl-4-[4-(5,9-dimethyl-decyloxy)-3-hydroxy-phenyl]-butan-1-ol |

Another aspect of the invention provides the compounds of Table 25:

TABLE 25

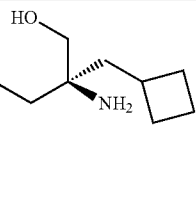

Compounds wherein $R^1$ is hydrogen or methyl, $R^2$ is 3-hydroxy, $R^3$ is cyclobutylmethyl.

| N & alkyl sidechain | | Name |
|---|---|---|
| n = 0, | 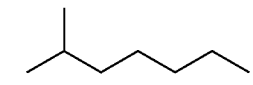 | (S)-2-Amino-2-cyclobutylmethyl-4-[4-(5-methyl-hexyloxy)-3-hydroxy-phenyl]-butan-1-ol |
| n = 1, | 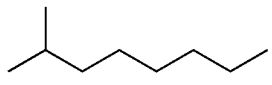 | (S)-2-Amino-2-cyclobutylmethyl-4-[4-(6-methyl-heptyloxy)-3-hydroxy-phenyl]-butan-1-ol |
| n = 2, | 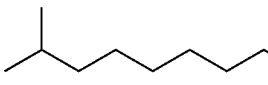 | (S)-2-Amino-2-cyclobutylmethyl-4-[4-(7-methyl-octyloxy)-3-hydroxy-phenyl]-butan-1-ol |
| n = 3, | 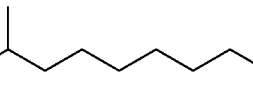 | (S)-2-Amino-2-cyclobutylmethyl-4-[4-(8-methyl-nonyloxy)-3-hydroxy-phenyl]-butan-1-ol |
| n = 4, | 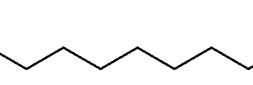 | (S)-2-Amino-2-cyclobutylmethyl-4-[4-(9-methyl-decyloxy)-phenyl]-3-hydroxy-butan-1-ol |
| n = 0, | 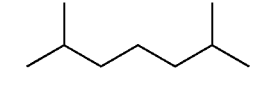 | (S)-2-Amino-2-cyclobutylmethyl-4-[4-(1,5-dimethyl-hexyloxy)-3-hydroxy-phenyl]-butan-1-ol |
| n = 1, | 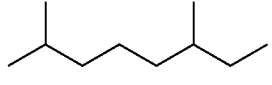 | (S)-2-Amino-2-cyclobutylmethyl-4-[4-(2,6-dimethyl-heptyloxy)-3-hydroxy-phenyl]-butan-1-ol |
| n = 2, | 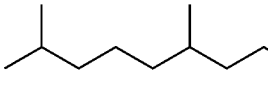 | (S)-2-Amino-2-cyclobutylmethyl-4-[4-(3,7-dimethyl-octyloxy)-3-hydroxy-phenyl]-butan-1-ol |
| n = 3, | 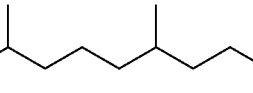 | (S)-2-Amino-2-cyclobutylmethyl-4-[4-(4,8-dimethyl-nonyloxy)-3-hydroxy-phenyl]-butan-1-ol |
| n = 4, | 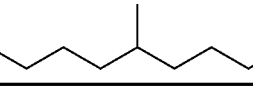 | (S)-2-Amino-2-cyclobutylmethyl-4-[4-(5,9-dimethyl-decyloxy)-3-hydroxy-phenyl]-butan-1-ol |

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Cancer Treatment Using the Compounds of the Invention

The present invention provides methods for treating or preventing the development of cancer in a subject by administering to the subject a pharmaceutical composition including a compound of formula I or a pharmaceutically acceptable salt thereof. Cancer is a disease of abnormal and excessive cell proliferation. Cancer is generally initiated by an environmental insult or error in replication that allows a small fraction of cells to escape the normal controls on proliferation and increase their number. The damage or error generally affects the DNA encoding cell cycle checkpoint controls, or related aspects of cell growth control such as tumor suppressor genes. As this fraction of cells proliferates, additional genetic variants may be generated, and if they provide growth advantages, will be selected in an evolutionary fashion. Cells that have developed growth advantages but have not yet become fully cancerous are referred to as precancerous cells. Cancer results in an increased number of cancer cells in a subject. These cells may form an abnormal mass of cells called a tumor, the cells of which are referred to as tumor cells. The overall amount of tumor cells in the body of a subject is referred to as the tumor load. Tumors can be either benign or malignant. A benign tumor contains cells that are proliferating but remain at a specific site and are often encapsulated. The cells of a malignant tumor, on the other hand, can invade and destroy nearby tissue and spread to other parts of the body through a process referred to as metastasis.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system. Examples of types of cancer that can be treated using the compounds of the present invention include cancer is selected from the group consisting of leukemia, hepatic cancer, non-small cell lung cancer, colon cancer, central nervous system cancer, melanoma, ovarian cancer, renal cancer, prostate cancer, and breast cancer.

Accordingly, in another aspect, the invention provides a method for treating or preventing cancer in a subject, that includes administering to the subject a pharmaceutical composition including a compound of formula I or a pharmaceutically acceptable salt thereof:

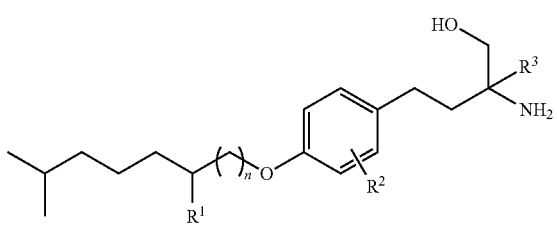

wherein $R^1$ is independently selected from the group consisting of hydrogen, methyl. methoxy, and hydroxyl; $R^2$ is independently selected from the group consisting of hydrogen, methoxy, and hydroxyl; $R^3$ is independently selected from the group consisting of alkyl and cyclo-alkyl; and n is independently selected from 0 to 6.

The pharmaceutical composition can also include any of the more specific embodiments of the compounds of formula I described herein. For example, the method of treatment can use the compound designated OSU-2S and having the structure:

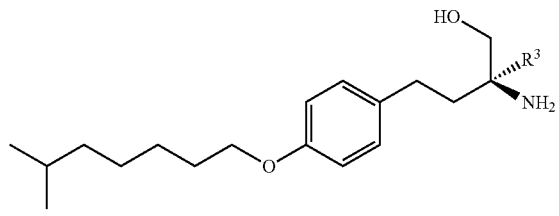

A preferred cancer for treatment by pharmaceutical compositions including a compound of formula I is hepatocellular carcinoma, due to the cellular resistance this type of cancer often has to many conventional cytotoxic agents. A preferred method of treatment of hepatocellular carcinoma using the compounds of the invention is their use in transarterial chemoembolization (TACE), which is a minimally invasive procedure useful for treating large or multifocal tumors that involves delivery of microspheres containing a pharmaceutical composition to blood vessels that feed the tumor. Because the compounds is delivered directly to the tumor rather than systemically, side effects can be lessened when using TACE.

Molecular-targeted therapies are an attractive treatment option for cancer, particular cancers such as hepatocellular carcinoma. Cancer can be treated or prevented by regulating signaling pathways within the cancerous or potentially cancerous cells to prevent excessive growth or provide regulation of other aberrant processes within the cells. While not intending to be bound by theory, the compounds of the present invention can treat or prevent cancer by activating Protein kinase C delta (PKCδ). As described in more detail in the Example, the compounds of formula I facilitate the activation of PKCδ through reactive oxygen species generation, leading to increased caspase 3 activity which in turn activated PKCδ via proteolytic cleavange, leading to an increase in cell apoptosis in cancer cells.

Beyond their anticancer activity, another advantage of many of the FTY720-derived compounds of the invention is their lower immunosuppressive activity. The parent compound FTY720 is transformed SphK2, which phosphorylates the compound before it exhibits its immunomodulating activity. The inventors have shown herein, however, that the FTY720-derived compounds of formula I are not phosphorylated by SphK2, which results in their not having the undesired immunomodulating effects. Accordingly, one aspect of the present invention provides a method of treating or preventing cancer in a subject using the compounds of formula I wherein the subject exhibits a low or nonexistent level of immunosuppression subsequent to administering the pharmaceutical composition The compounds of the invention can be used to provide prophylactic and/or therapeutic treatment. The compounds of the invention can, for example, be administered prophylactically to a subject in advance of the occurrence of cancer. Prophylactic (i.e., preventive) administration is effective to decrease the likelihood of the subsequent occurrence of cancer in the subject, or decrease the severity of cancer that subsequently occurs. Prophylactic treatment may be provided to a subject that is at elevated risk of developing cancer, such as a subject with a family history of cancer or exposure to high levels of carcinogens. The expression levels of PKCδ and GST-π represent two key determinants for cellular sensitivity to the compounds of formula I, and thus their levels may be useful as criteria for selecting patients to receive anticancer therapy; e.g., OSU-2S would benefit HCC patients with moderate to high PKCδ and low GST-π expression.

Alternatively, the compounds of the invention can, for example, be administered therapeutically to a subject that is already afflicted by cancer. In one embodiment of therapeutic administration, administration of the compounds is effective to eliminate the cancer; in another embodiment, administration of the compounds is effective to decrease the severity of the cancer or lengthen the lifespan of the subject so afflicted. The subject is preferably a mammal, such as a domesticated farm animal (e.g., cow, horse, pig) or pet (e.g., dog, cat). More preferably, the subject is a human.

Administration and Formulation of the Compounds of the Invention

The present invention also provides pharmaceutical compositions that include compounds such as those defined by formula I as an active ingredient, and a pharmaceutically acceptable liquid or solid carrier or carriers, in combination with the active ingredient. Any of the compounds described above as being suitable for the treatment of cancer can be included in pharmaceutical compositions of the invention.

The compounds can be administered as pharmaceutically acceptable salts. Pharmaceutically acceptable salt refers to the relatively non-toxic, inorganic and organic acid addition salts of the compounds. These salts can be prepared in situ during the final isolation and purification of the compounds of the invention, or by separately reacting a purified compound of the invention with a suitable counterion, depending on the nature of the compound, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions include one or more compounds of the invention together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the compound, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The formulated compounds can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the active compound, or as a solution or suspension in an aqueous liquor or non-aqueous liquid such as a syrup, an elixir, an emulsion, or a draught. Such compositions and preparations typically contain at least about 0.1 wt-% of the active agent. The amount of the compound of the invention (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie,* 4, Aufl. Ed. Springer-Verlag, Berlin, Germany, including supplements (also available via the Beilstein online database)).

Figure 8:
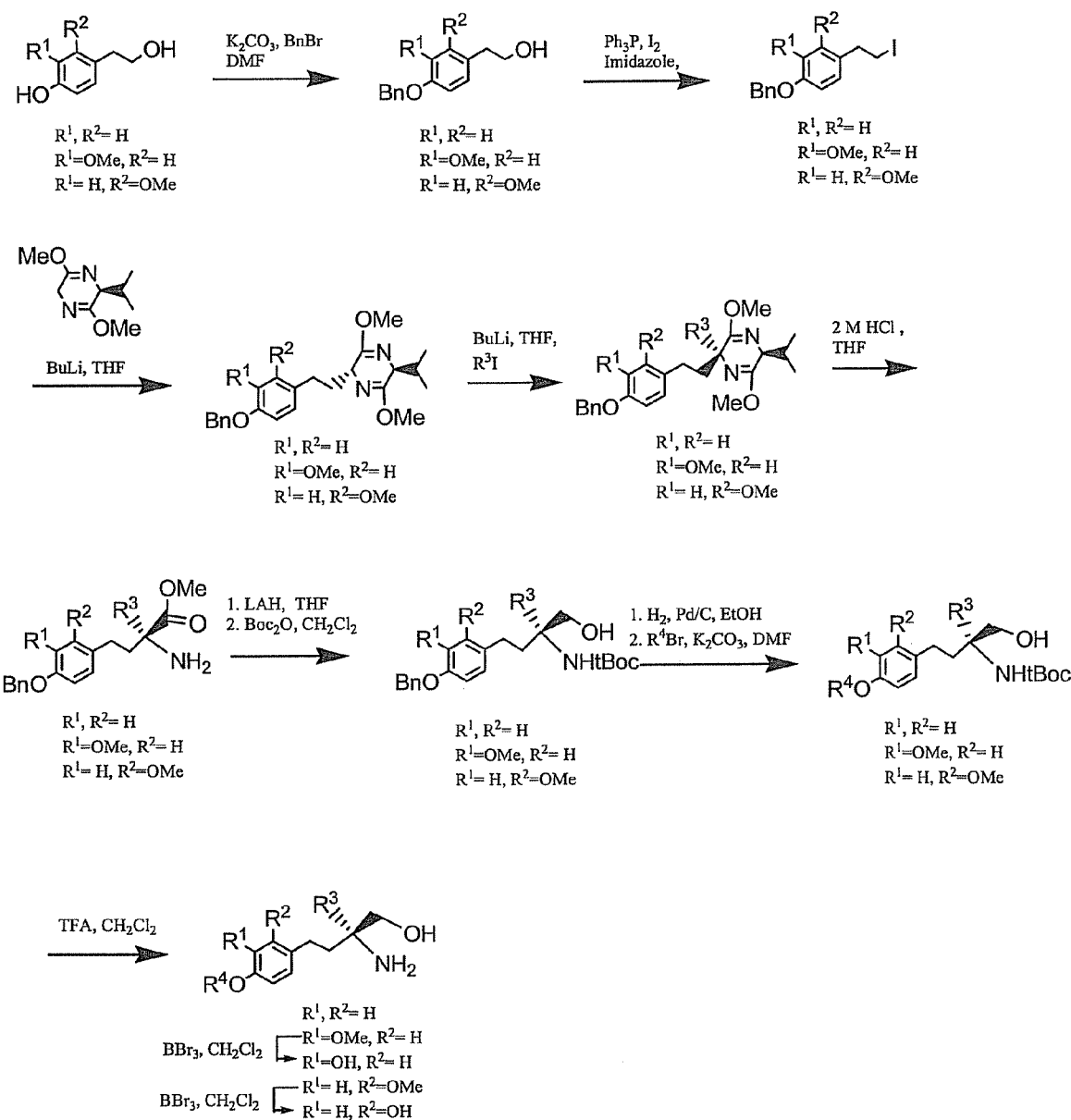
FIG. 8 provides a general synthetic scheme for the preparation of FTY720-derived compounds of the present invention.

FIG. 8 illustrates a general synthetic scheme for preparing FTY720-derived compounds of the present invention. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

General Procedure for the Synthesis of FTY720-Derived Compounds

The benzylation of the phenol group is shown in Scheme I:

Scheme I

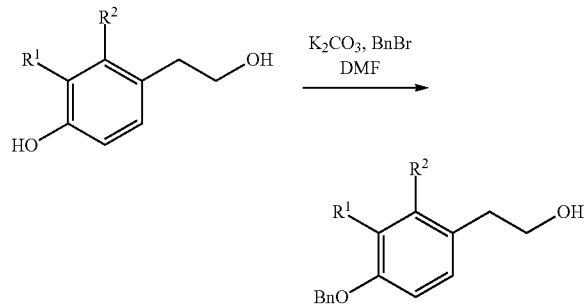

A mixture of 4-hydroxyethyl phenol (10 mmol), benzyl bromide (11 mmol) and potassium carbonate (15 mmol) in DMF was stirred at 60° C. overnight. The resulting reaction mixture was cooled to room temperature (r.t.) and poured into water and extracted with ethyl acetate (3×50 mL). The combined organic layers were washed with water and brine, dried with sodium sulfate, filtered and the filtrate was concentrated. The residue was purified using a silica gel column to provide the pure benzylated product.

Preparation of Iodide from Alcohol is Shown in Scheme II:

Scheme II

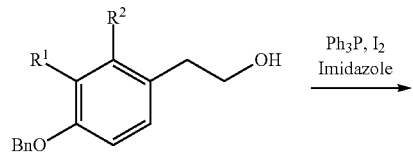

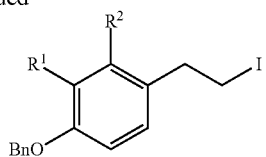

To a solution of triphenyl phosphine (12.2 mmol) in dichloromethane, $I_2$ (12.2 mmol) was added and the reaction mixture was stirred for another 10 min. after addition. Imidazole (12.2 mmol) was added and stirred for 10 more min. before addition of benzylated product (9 mmol) from the previously described procedure. The resulting reaction mixture was stirred for 5 hr, washed with water, 10% sodium thiosulfite and brine, dried with sodium sulfate, filtered and the filtrate was concentrated. The residue was purified with silica gel column to provide the Iodide product.

The first alkylation of the (S)-Schollkopf reagent is shown in Scheme III:

Scheme III

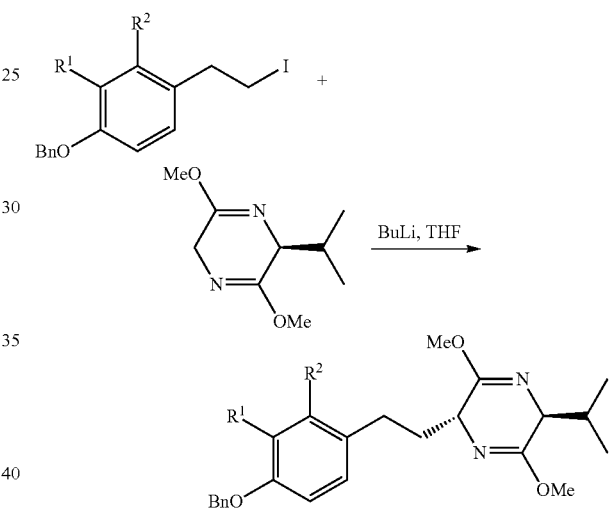

To a solution of (S)-Schollkopf reagent (8 mmol) in dry THF, butyl lithium (5 mL, 1.6 M in hexane) was added slowly at −70° C. and then stirred for 30 min at same temperature. The iodide compounds (8.8 mmol) in THF was added slowly at −70° C. The final reaction mixture was stirred for another 5 hrs and then stirred overnight at 0-70° C. Saturated ammonium chloride solution was added, organic layer was separated, the aqueous layer was extracted with ethyl acetate (2×50 mL) and the combined organic layers were washed with brine, dried with sodium sulfate, filtered and the filtrate concentrated. The residue was purified with silica gel column to provide the pure alkylation product.

The second alkylation at 6 position of (S)-Schollkopf reagent is shown in Scheme IV:

Scheme IV

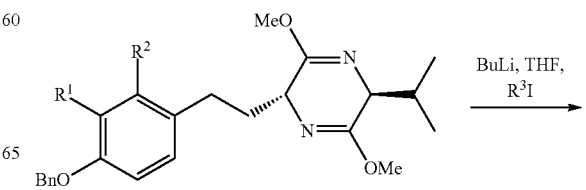

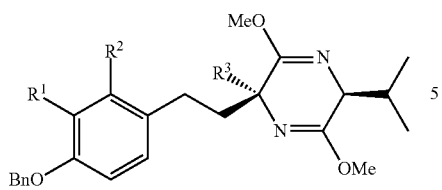

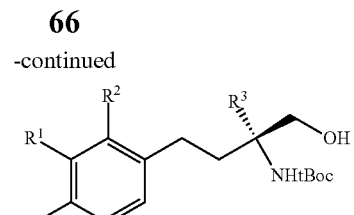

To a solution of the alkylation product from previous procedure (6 mmol) in dry THF, butyl lithium (3.8 mL, 1.6 M in hexane) was added slowly at −70° C. The resulting reaction mixture was then stirred for another 30 min at same temperature. Alkyl iodide (6.6 mmol) in dry THF was added slowly at −70° C., stirred for 5 hrs and then warmed up to 0° C. and stirred overnight. Saturated ammonium chloride solution was added, the organic layer was separated, the aqueous layer was extracted with ethyl acetate (2×50 mL) and the combined organic layers were washed with brine, dried with sodium sulfate, filtered and the filtrate concentrated. The residue was purified using a silica gel column to provide the pure product.

Acid hydrolysis of alkylated (S)-Schollkopf reagent is shown in Scheme V:

The amino product (3 mmol) from last step was treated with LiAlH$_4$ in dry THF at 0° C. for 3 hrs. The excess amount of LiAlH$_4$ was decomposed with slowly adding water. The resulting reaction mixture was filtered and the filtrate was dried with sodium sulfate and concentrated. The crude product was directly treated with di-tert-butyl-dicarbonate (3.75 mmol) in dichloromethane at room temperature overnight. The resulting reaction mixture was washed with water and brine, dried with sodium sulfate, filtered and the filtrate was concentrated. The residue was purified with silica gel column gave pure Boc protected amino product.

Deprotection of phenol group followed by alkylation with alkyl bromide is shown in Scheme VII:

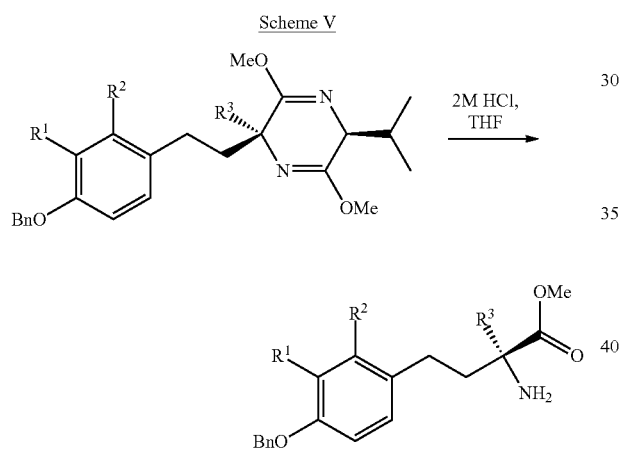

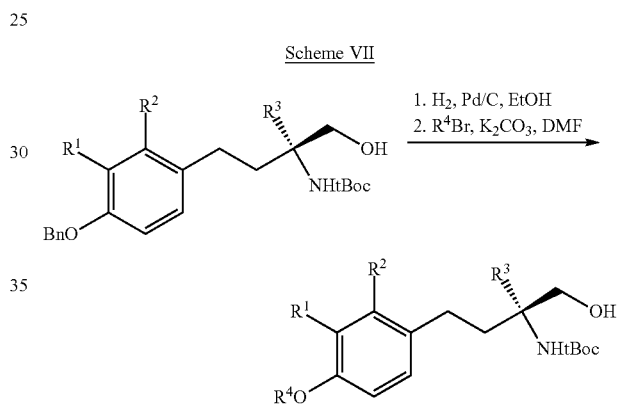

The mixture of alkylation product from previous procedure (4.5 mmol) and 2M HCl in THF was stirred overnight. The resulting reaction mixture was neutralized with 10% sodium carbonate solution and extracted with ethyl acetate (3×30 mL). The combined organic layers were washed with brine, dried with sodium sulfate, filtered and the filtrate was concentrated. The residue was purified using a silica gel column to give the pure amino product.

Reduction of ester group with LAH followed by tBoc protection of amino group is shown in Scheme VI:

The tBoc protected amino product (2.5 mmol) from previous procedure was treated with 10% Pd/C and hydrogen at 55 psi for 5 hrs. The resulting reaction mixture was filtered and the filtrate was concentrated. The crude product was directly reacted with alkyl bromide or iodide without purification. Thus, the mixture of hydrogenation product (0.2 mmol), potassium carbonate (0.3 mmol), and alkyl bromide (0.3 mmol) in DMF was stirred at 65° C. overnight. The resulting reaction mixture was poured into ice water and extracted with ethyl acetate (3×25 mL). The combined organic layer was washed with water and brine, dried with sodium sulfate, filtered and the filtrate was concentrated. The residue was purified using a silica gel column to provide the pure product.

Alkylation with alkyl iodide is shown in Scheme VIII:

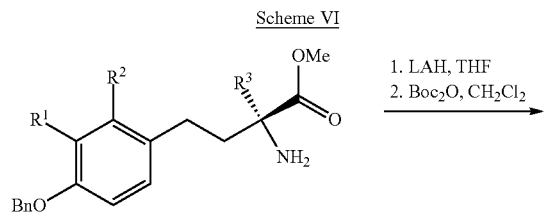

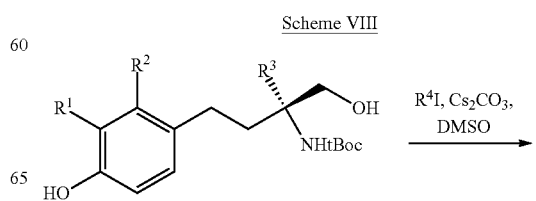

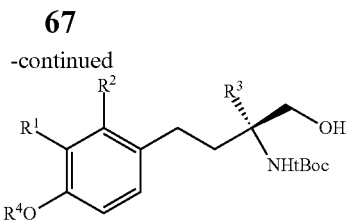

The mixture of hydrogenation product (0.2 mmol), cesium carbonate (0.3 mmol), and alkyl iodide (0.3 mmol) in DMSO was stirred at 55° C. overnight. The resulting reaction mixture was poured into ice water and extracted with ethyl acetate (3×25 mL). The combined organic layer was washed with water and brine, dried with sodium sulfate, filtered and the filtrate was concentrated. The residue was purified using a silica gel column to give the pure product.

Amino deprotection with trifluoracetic acid (TFA) is shown in Scheme IX:

Scheme IX

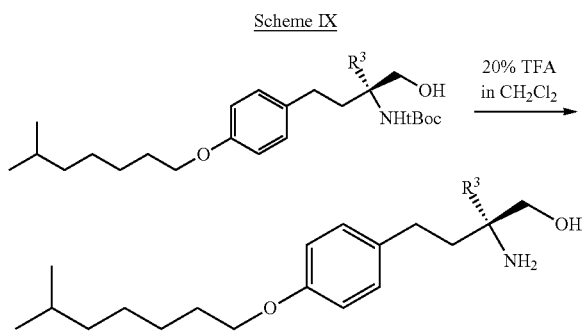

The mixture of tBoc protected compound (0.1 mmol) and 20% TFA in dichloromethane was stirred at room temperature for 3 hrs. The resulting reaction mixture was neutralized to pH 9 with 10% sodium carbonate solution. The separated aqueous layer was extracted with dichloromethane 2×15 mL) and the combined organic layers were dried with sodium sulfate, filtered and the filtrate was concentrated. The residue was purified using a silica gel column to give the pure product.

Amino deprotection with TFA is shown in Scheme X:

Scheme X

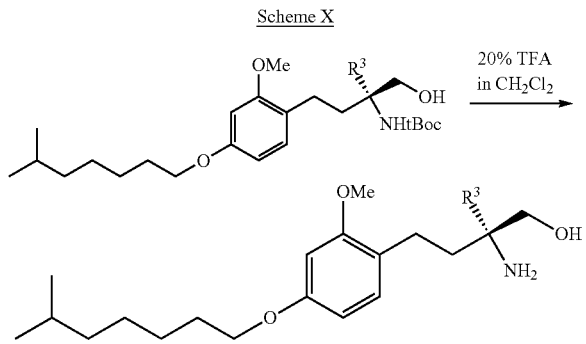

The mixture of tBoc protected compound (0.1 mmol) and 20% TFA in dichloromethane was stirred at room temperature for 3 hrs. The resulting reaction mixture was neutralized to pH 9 with 10% sodium carbonate solution. The separated aqueous layer was extracted with dichloromethane (2×15 mL) and the combined organic layers were dried with sodium sulfate, filtered and concentrated. The residue was then purified using a silica gel column to give the pure product.

Deprotection of the methoxy group and the tBoc group are shown in Scheme XI:

Scheme XI

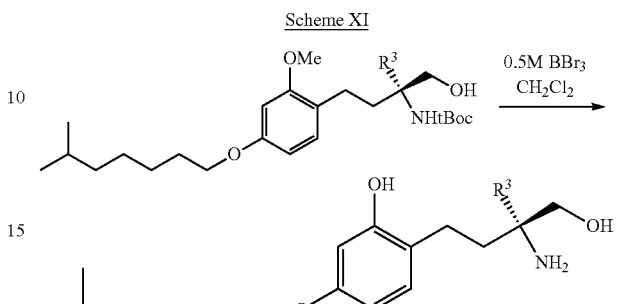

To a solution of tBoc protected amino compound (0.1 mmol) in dichloromethane (5 mL), $BBr_3$ solution in dichloromethane (1 M, 5 mL) was added at 0° C. and the resulting reaction mixture was stirred at room temperature for 3 hrs and then poured into 1N HCl solution. The acid solution was then neutralized to pH 9 and extracted with dichloromethane (3×15 mL). The combined organic layers were washed with water and brine, dried with sodium sulfate, filtered and the filtrate was concentrated. The residue was purified using a silica gel column to give the pure product.

Example 2

Antitumor Effects of OSU-2S, a Non-Immunosuppressive Analogue of FTY720, in Hepatocellular Carcinoma Previously, the inventors demonstrated that FTY720 induces apoptosis in HCC cells through the reactive oxygen species (ROS)-dependent activation of protein kinase C (PKC)δ. Hung et al., Cancer Res, 68, 1204-1212 (2008). Dissociation of the apoptosis-inducing activity of FTY720 from its S1P receptor agonist activity provides a basis for its pharmacological exploitation to develop a novel class of antitumor agents. Herein the inventors report the development of a non-immunosuppressive FTY720 analogue, OSU-2S [(S)-2-amino-2-(4-[(6-methylheptyl)-oxy]phenethyl)pentan-1-ol], which exhibits higher in vitro and in vivo potency than FTY720 in suppressing HCC cell growth through PKCδ signaling.

Experimental Procedures

Cell lines, culture and reagents. The HCC cell lines Hep3B, PLC5 and Huh7, as well as primary nonmalignant human hepatocytes were used in this study. Cancer cells were cultured in Dulbecco's Modified Eagle's medium (DMEM) supplemented with 10% fetal bovine serum (FBS). Hepatocytes were maintained in defined Hepatocyte Culture Medium. FTY720 was synthesized as described (Kiuchi et al., J Med Chem 43, 2946-2961 (2000)), and p-FTY720 was purchased from Cayman Chemicals (Ann Arbor, Mich.). Various polyclonal and monoclonal antibodies were used for western blotting, immunocytochemical, and flow cytometric analyses.

Cell viability assay. Cell viability was assessed by 3-(4,5-dimethylthiazol-2-yl)-2,5-diphenyl-2H-tetrazolium bromide (MTT) assays in six replicates. Cells were seeded (4,000 cells/well; 96-well plate) for 24 h and treated with test agents in 5% FBS-supplemented DMEM. After treatment, cells were incubated in medium containing 0.5 mg/ml MTT (37° C., 2 h). Reduced MTT was dissolved in DMSO (200 µL/well) and absorbances measured at 570 nm.

Flow cytometry. For assessment of apoptosis, treated cells were stained with Annexin V-Alexa Fluor 488 and propidium iodide according to the vendor's protocols (Molecular Probes). For caspase-3 activity, cells were incubated with the fluorogenic caspase-3 substrate (Ac-DMQD)-2-Rh110 for 20 min. ROS production was detected using the fluorescence probe 5-(and-6)-carboxy-2',7'-dichlorodihydrofluorescein diacetate (DCFDA) as described. Hung et al., Cancer Res., 68, 1204-1212 (2008). Data were analyzed by ModFitLT V3.0 software program.

Immunoblotting. Immunoblotting of biomarkers in cell lysates and tumor tissue homogenates was carried out according to a published procedure. Hung et al., Cancer Res., 68, 1204-1212 (2008).

Small interfering (si)RNA- or short hairpin (sh)RNA-mediated knockdown. PLC5 and Huh7 cells were transfected with the following siRNA duplexes or shRNA plasmids according to the manufacturer's protocol for the knockdown of target genes: siRNA: glutathione S-transferase (GST)-π and sphingosine kinase 2 (SphK2); shRNA constructs: pKD-PKCδ-v2. Stable clones were isolated from Huh7 cells transfected with shRNA plasmids were further subjected to stable clone isolation by geneticin. Immunoblotting was performed to confirm the knockdowns.

Overexpression of S1P1 Receptors. Huh7 or Hep3B cells were transfected with plasmids encoding S1PR1, Flag-tagged GST-π or hemagglutinin (HA)-tagged, CA-Akt. The corresponding empty vectors were used as controls. Stable clones were selected over 3 weeks by geneticin, and the expression of cloned proteins was confirmed by Western blotting.

Phosphorylation of FTY720 and OSU-2S by SphK2. Analysis of SphK2-mediated phosphorylation was performed as reported with modifications. Prieschl 32323345yuioyuio J Exp Med, 190, 1-8 (1999). Briefly, 5 µM FTY720 or OSU-2S was incubated with 0.75 µg/ml human recombinant SphK2 (Cayman), 5 µCi $[\gamma-^{32}P]$-ATP, and 0.5 mM cold ATP at 37° C. for 60 min. The reaction products were separated by silica-gel thin layer chromatography (TLC) and visualized by autoradiography.

Immunocytochemistry. Immunocytochemical analysis of S1P1 internalization and PKCδ nuclear translocation were performed as described. Tseng et al., Mol Pharmacol 70, 1534-1541 (2006). Briefly, treated cells were washed, fixed with 4% paraformaldehyde, and permeabilized with 0.1% Triton X-100. After blocking with 2% FBS, cells were incubated with rabbit anti-S1P1 or rabbit anti-PKCδ antibodies (1:200 dilution, 4° C., 24 h), followed by Alexa Fluor 488-conjugated goat anti-rabbit IgG (room temperature, 1 h). Nuclei were counterstained with a 4,6-diamidino-2-phenylindole (DAPI)-containing mounting medium (Vector Laboratories, Burlingame, Calif.).

In vivo evaluation of T-lymphocyte homing. CD2F1 mice were treated via intraperitoneal (i.p.) injection with FTY720 or OSU-2S, at 1, 2.5, or 5 mg/kg, or vehicle (sterile saline containing 0.5% Tween-80). Six hours later, animals were sacrificed, and peripheral blood mononuclear cells were prepared as described. Dragun et al., Kidney Int 65, 1076-1083 (2004). Cells were stained with FITC-labeled rat anti-mouse CD3 molecular complex and PE-labeled rat anti-mouse CD45RA (4° C., in darkness, 30 min), and analyzed by flow cytometry.

Xenograft tumor models. Ectopic tumors were established in athymic nude mice by subcutaneous injection of $1\times10^6$ Hep3B cells in a total volume of 0.1 ml of serum-free medium containing 50% Matrigel. Mice with established tumors were randomized to five groups (n=8) that received daily i.p. injections of OSU-2S or FTY720 at 5 or 10 mg/kg, or the vehicle. Tumor burdens were determined weekly using calipers (volume=width$^2$×length×0.52). Body weights were measured weekly. At the study endpoint, tumors were harvested, snap-frozen and stored at −80° C. for biomarker analysis. Blood and tissues were collected for evaluation of complete blood counts, serum chemistry and histopathology.

Orthotopic tumors were established by direct intrahepatic injection of luciferase-expressing Hep3B (Hep3B-luc) cells as described. Omar et al., Mol Pharmacol, 76, 957-968 (2009). The establishment and growth of tumors were monitored by bioluminescent imaging using the IVIS™ imaging system (Xenogen, Alameda, Calif.). Two weeks after tumor cell injection, animals with established tumors were randomized to three groups (n=3) that received daily i.p. injections of FTY720 or OSU-2S at 5 mg/kg, or vehicle for 42 days and were imaged weekly. All animal use described in this manuscript was done in accordance with protocols approved by The Ohio State University Institutional Animal Care and Use Committee.

Expression of PKCδ in HCC and non-neoplastic human liver tissues. A tissue microarray (TMA) containing both HCC and non-neoplastic liver tissues was constructed from archival paraffin-embedded tissue samples as described. Baumhoer et al., Am J Clin Pathol, 129, 899-906 (2008). The TMA was immunostained for PKCδ at the OSUCCC Comparative Pathology and Mouse Phenotyping Shared Resource. PKCδ expression was evaluated in 163 HCC and 71 non-neoplastic liver samples using a semi-quantitative scoring system (0, negative; 1, weak; 2, moderate; 3, strong).

Statistical analysis. Differences among group means were analyzed for statistical significance using one-way analysis of variance followed by the Neuman-Keuls test for multiple comparisons. Differences in the proportions of PKCδ-positive HCC and non-neoplastic liver samples were analyzed by Fisher's exact test. Differences were considered significant at $P<0.05$. Statistical analysis was performed using GraphPad InStat™ for Windows (GraphPad Software, San Diego, Calif.).

Results

OSU-2S, a non-immunosuppressive FTY720 analogue with higher antiproliferative potency in HCC cells. Based on the finding that the antitumor effect of FTY720 in HCC cells was mediated through PKCδ activation, the inventors hypothesized that these two pharmacological activities, i.e., immunosuppression versus anti-proliferation, could be dissociated via structural modifications. Thus, FTY720 was used as scaffold to establish a small focused compound library for lead identification. Among more than 20 derivatives examined, OSU-2S (structure, FIG. 1A) lacked immunomodulatory activity, yet exhibited higher potency than FTY720 in inducing apoptotic death in HCC cells, thereby providing a proof-of-concept of the inventors' hypothesis.

It is well recognized that FTY720 acts as a prodrug that undergoes phosphorylation by SphK2 to mediate its immunomodulatory function. Brinkmann et al., J Biol Chem, 277, 21453-21457 (2002). Radiometric analysis, followed by TLC, revealed that, in contrast to FTY720, OSU-2S was not phosphorylated by recombinant SphK2 (FIG. 1B). Although OSU-2S was not a substrate for SphK2, its phosphate derivative, p-OSU-2S, was synthesized to test its ability vis-à-vis p-FTY720, FTY720, and OSU-2S to facilitate the internalization of S1P receptors, a key mechanism underlying FTY720-mediated immunomodulation (Mullershausen et al., Nat Chem Biol, 5, 428-434 (2009)), in S1P1 receptor-overexpressing Huh7 cells. Immunocytochemical analysis indicated a profound effect of FTY720 and p-FTY720 on receptor internalization and clustering in the cytoplasm, while OSU-2S or p-OSU-2S failed to show any appreciable effect. To confirm these results, in vivo analysis of the effects of these agents on T-lymphocyte homing was performed in CD2F1 mice. Treatment with FTY720 for 6 h, even at 1 mg/kg, caused a precipitous drop ($\geq$75%) in the number of T lymphocytes in peripheral blood, while OSU-2S exerted no appreciable effect at 1 and 2 mg/kg and a modest decrease at 5 mg/kg (FIG. 1C). As OSU-2S and p-OSU-2S had no effect on S1P1 receptor internalization, the reason for this modest suppression in circulating T lymphocytes is unclear; however, it appears to be a transient change, since no decrease in total lymphocyte counts was noted in OSU-2S-treated mice after 42 days of treatment. In contrast, no comparable changes were noted with either agent in circulating B lymphocytes.

Figure 2:
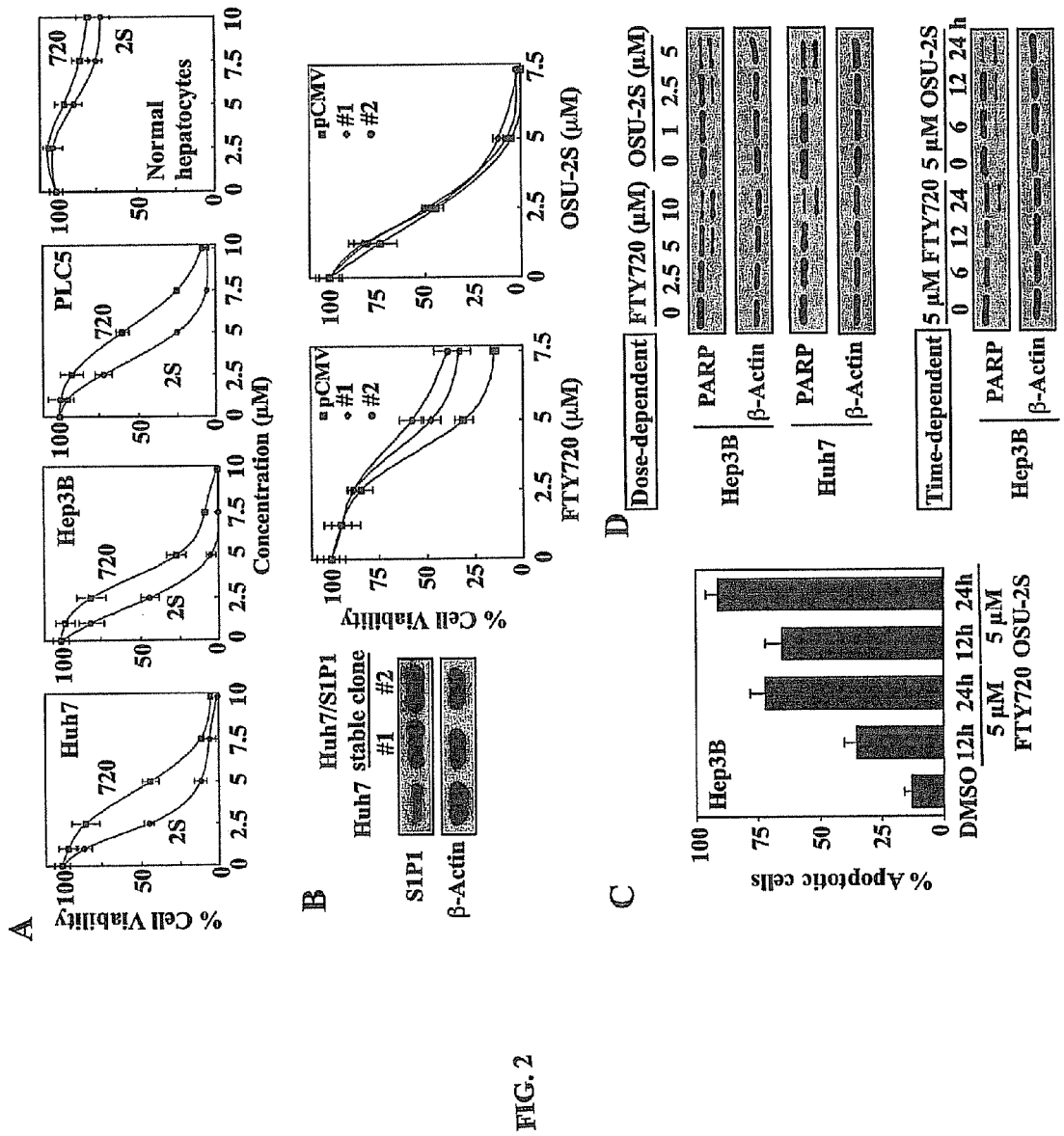
FIG. 2 provides graphs and data showing that OSU-2S exhibits a higher potency than FTY720 in inducing apoptotic death in HCC cells independent of sphingosine-1-phosphate 1 (S1P1) receptor agonist activity. Section (A) shows the dose-dependent suppressive effects of OSU-2S (2S) and FTY720 (720) on the viability of Huh7, Hep3B, and PLC5 cells relative to normal human hepatocytes after 24 h of treatment. Points, mean; bars, ±SD (n=6). Section (B) shows the effect of ectopic S1P1 receptor expression on the sensitivity of Huh7 cells to FTY720-versus OSU-2S-mediated inhibition of cell viability. Left, Western blot analysis of the differential expression levels of S1P1 receptors in untransfected Huh7 cells versus two stable S1P1 receptor transfectants. Right, effect of FTY720 and OSU-2S on the viabilities of untransfected Huh7 cells and stable S1P1 receptor-overexpressing clones (#1 and #2). Points, mean; bars, ±SD (n=6). Section (C) shows the results of flow cytometric analysis of apoptosis in Hep3B cells treated with 5 µM of FTY720 or OSU-2S for 12 and 24 h. The cells were stained with fluorescein-conjugated Annexin V and propidium iodide (PI). Apoptotic cells included both Annexin V+/PI− (early apoptotic) and Annexin+/PI+ (late apoptotic) cells. Columns, mean; bars, SD (n=3). Section (D) shows the Western blot analysis of the dose- and time-dependent effects of FTY720 and OSU-2S on poly (ADP-ribose) polymerase (PARP) cleavage in Hep3B and Huh7 cells.

The antitumor effects of OSU-2S vis-à-vis FTY720 were examined in three different HCC cell lines, Huh7, Hep3B, and PLC5, and compared to the effects in normal human hepatocytes by MTT assays. OSU-2S exhibited nearly two-fold higher potency than FTY720 in suppressing the viability of these HCC cells (FIG. 2A). The $IC_{50}$ values in Huh7, Hep3B, and PLC5 cells after 24 h of treatment were: OSU-2S: 2.4 µM, 2.4 µM, and 3.5 respectively; FTY720: 4.8 µM, 4.2 µM, and 6.2 respectively. Relative to malignant cells, normal human hepatocytes were resistant to both compounds. This discriminative antiproliferative effect underscores the unique mode of antitumor action of these two agents.

As mentioned above, OSU-2S exhibits higher antitumor activity than FTY720 despite lacking immunosuppressive activity. To demonstrate that its antitumor effect was independent of S1P1 receptors, the inventors evaluated the effect of ectopic S1P1 receptor expression on the antiproliferative activities of OSU-2S vis-à-vis FTY720 in Huh7 cells. Two stable clones exhibiting different levels of ectopic S1P1 receptor expression and wild-type Huh7 cells were treated with different concentrations of FTY720 or OSU-2S. While S1P1 receptor overexpression partially protected Huh7 cells against FTY720 in an expression level-dependent manner, no protective effect was noted in OSU-2S-treated cells (FIG. 2B). As evidenced by Annexin V/PI staining and PARP cleavage, OSU-2S mediated cell death primarily through apoptosis in a manner similar to FTY720 with relative potency paralleling that determined by MTT assays (FIGS. 2C & D).

Figure 3:
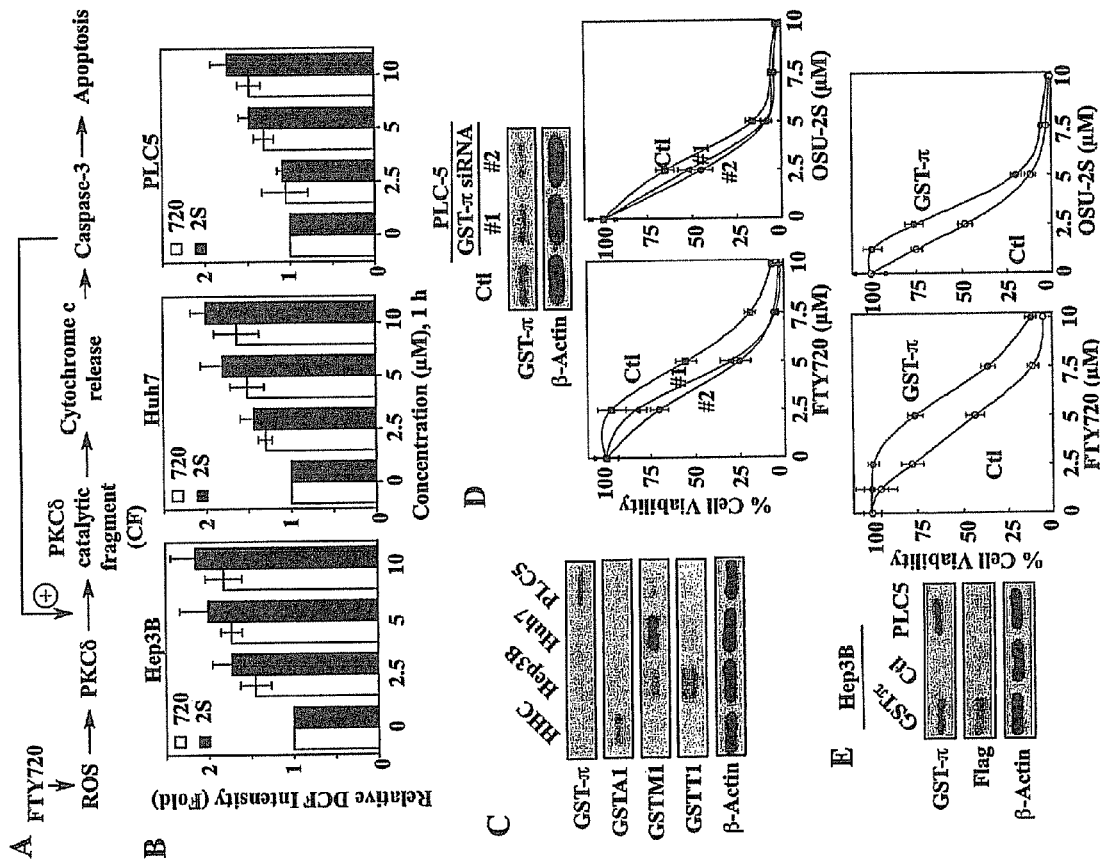
FIG. 3 provides graphs and data showing that the reactive oxygen species (ROS)-PKCδ signaling pathway is involved in OSU-2S-mediated apoptosis in HCC cells. Section (A) provides a schematic diagram depicting the mode of action of FTY720 in eliciting PKCδ-dependent apoptosis. Section (B) shows the dose-dependent effect of OSU-2S (2S) versus FTY720 (720) on ROS production in Hep3B, Huh7, and PLC5 cells after 1 h of treatment. DCF, dichlorofluorescein. Columns, mean; bars, ±SD (n=3). Section (C) shows the Western blot analysis of the expression of the four GST isozymes (GST-π, GSTA1, GSTM1, and GSTT1) in normal human hepatocytes (HHC), Hep3B, Huh7, and PLC5 cells. Section (D) shows the effect of siRNA-mediated GST-π knockdown on the sensitivity of PLC5 cells to FTY720 and OSU-2S. Upper, differential expression of GST-π in PLC5 cells transiently transfected with scrambled (Ctl) or GST-n siRNA (#1 and #2). Lower, the antiproliferative activities of FTY720 and OSU-2S in the two GST-n siRNA transfectants (#1 and #2) versus control (Ctl) cells. Points, mean; bars, ±SD (n=6). Section (E) shows the effect of ectopic expression of GST-π on the sensitivity of Hep3B cells to FTY720 and OSU-2S. Left, expression levels of GST-π in Hep3B cells transiently transfected with a Flag-GST-π plasmid versus untransfected Hep3B (Ctl) and PLC5 cells. Middle and right panels, the antiproliferative activities of FTY720 and OSU-2S in GST-π-overexpressing Hep3B cells versus control. Points, mean; bars, ±SD (n=6).

OSU-2S induces caspase-dependent apoptosis through ROS-dependent PKCδ activation. The inventors have previously demonstrated that FTY720 facilitates ROS-dependent PKCδ activation, leading to increased caspase-3 activity, which, in turn, activates PKCδ via proteolytic cleavage in HCC cells (FIG. 3A). Hung et al., Cancer Res., 68, 1204-1212 (2008). The inventors obtained the following evidence that this signaling axis also underlies OSU-2S-mediated apoptosis.

Flow cytometry analysis using the ROS-sensitive probe DCFDA showed that OSU-2S stimulated ROS production to a greater extent than FTY720 in all three HCC cell lines examined (FIG. 3B). Moreover, the degree to which these two agents induced ROS levels paralleled their relative antiproliferative potencies in these cell lines, i.e., Hep3B>Huh7>PLC-5. The inventors rationalized that the differential induction of ROS production resulted from differences in the enzyme antioxidant capacity among these cell lines. Of the four representative GST isozymes examined (GST-π, GSTA1, GSTM1, and GSTT1), the expression levels of GST-π in Hep3B, Huh7, and PLC5 cells showed an inverse relationship with their respective sensitivities to FTY720- and OSU-2S-induced cell death (FIG. 3C versus FIG. 2A). For example, PLC5 cells, which exhibited the highest GST-π expression, were least sensitive among these three cell lines. These findings are consistent with the notion that GST-π represents a marker of drug resistance in HCC. Yusof et al., Anal Quant Cytol Histol, 25, 332-338 (2003). In contrast, normal human hepatocytes expressed low GTS-π levels, suggesting a different, GST-independent basis for their resistance to these compounds.

To validate the relationship between GST-π and drug resistance, the inventors evaluated the effects of altering GST-π expression through genetic manipulations on drug sensitivity. First, exposure of PLC5 cells to GST-π siRNA generated two transient transfectants exhibiting different levels of target suppression relative to the scrambled siRNA control (FIG. 3D, upper panel). As shown, knockdown of GST-π shifted the dose-response curves of OSU-2S and FTY720 to the left in both transfectants (lower panel). Second, ectopic expression of GST-π in Hep3B cells via transient transfection with a Flag-tagged GST-π plasmid (FIG. 3E, left panel) conferred protection against the suppressive effect of FTY720 and OSU-2S on cell viability (right panel).

Figure 4:
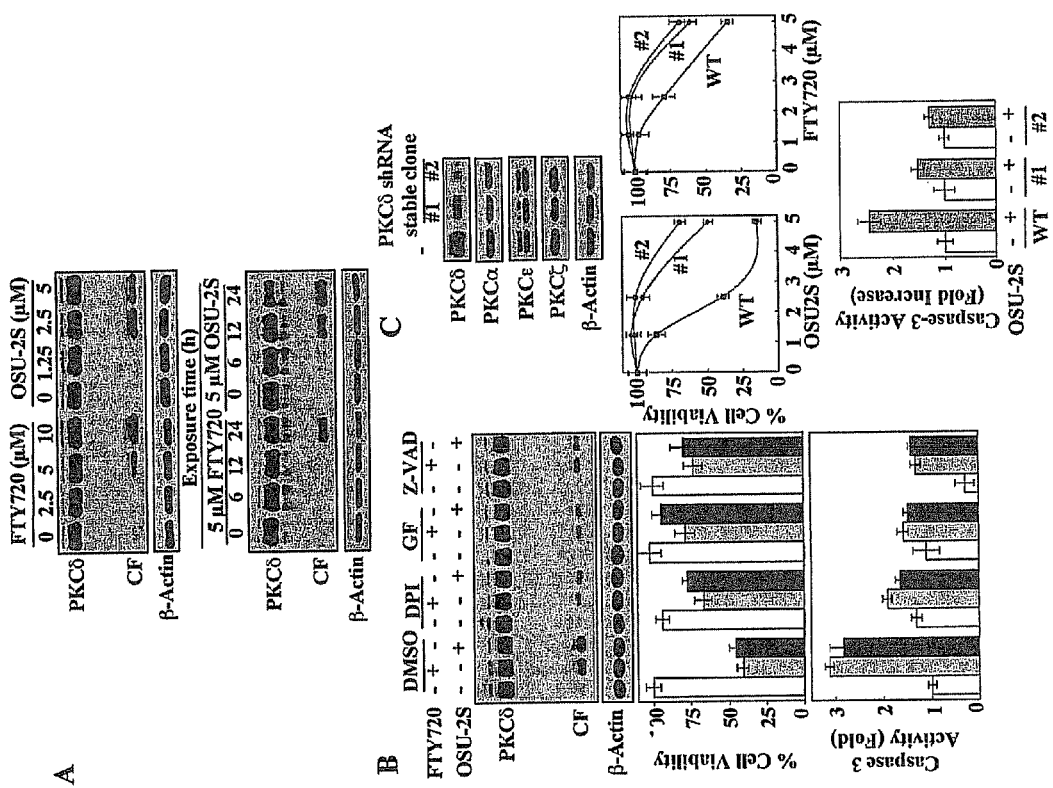
FIG. 4 provides graphs and data showing the role of PKCδ-caspase-3 signaling in mediating the antiproliferative effect of OSU-2S. Section (A) shows the dose-(upper panel) and time-dependent (lower panel) effects of FTY720 and OSU-2S on the activation of PKCδ by proteolytic cleavage in Huh7 cells as indicated by the appearance of the catalytic fragment (CF). Section (B) shows the effects of the pharmacological inhibitors of NADPH oxidase (diphenyleneiodonium [DPI], 10 µM), PKCδ (GF-109293×[GF], 5 µM), and caspases (Z-VAD-FMK [Z-VAD], 20 µM) on the abilities of FTY720 (5 µM) and OSU-2S (2.5 µM) to induce PKCδ activation (top), to suppress cell viability (middle), and to enhance caspase-3 activity (lower) in Huh7 cells. CF, catalytic fragment. Columns, mean; bars, ±SD (n=6). Section (C) shows that knockdown of PKCδ expression diminishes the ability of FTY720 and OSU-2S to mediate cell death and caspase-3 activation in Huh7 cells. Upper panel, Western blot analysis of shRNA-mediated knockdown of PKCδ in Huh7 cells showing the expression levels of PKCδ, PKCα, PKCε, and PKCζ in two stable clones (#1, #2) relative to the untransfected control. Central panel, knockdown of PKCδ protects Huh7 cells from FTY720- and OSU-2S-mediated suppression of cell viability. WT, wild-type. Points, mean; bars, ±SD (n=6). Lower panel, knockdown of PKCδ protected Huh7 cells from OSU-2S-induced activation of caspase-3 activity. Columns, mean; bars, ±SD (n=6).

The stimulation of ROS generation by FTY720 and OSU-2S was accompanied by PKCδ activation in Huh7 cells with parallel potency, as manifested by nuclear translocation (FIG. 4A) and dose- and time-dependent accumulation of the catalytic fragment in drug-treated Huh7 cells (FIG. 4A). Translocation of PKCδ to the nucleus and subsequent proteolytic cleavage have been shown to be necessary and sufficient to induce apoptosis in cancer cells. Reyland M E. Biochem Soc Trans, 35, 1001-1004 (2007). The role of the ROS-PKCδ-caspase-3 signaling axis in mediating OSU-2S's antiproliferative effect was further corroborated by the use of pharmacological inhibitors of pertinent cellular responses, i.e., the NADPH oxidase inhibitor diphenyleneiodonium (DPI), the PKCδ inhibitor GF-109293X, and the pan-caspase inhibitor Z-VAD-FMK. As shown, these inhibitors blocked the abilities of OSU-2S (2.5 µM) and FTY720 (5 µM) to induce the proteolytic cleavage of PKCδ (FIG. 4B, upper panel), to suppress cell viability (central panel), and to stimulate caspase-3 activity (lower panel). From a mechanistic perspective, the ability of DPI to protect cells from these drug effects suggests the involvement of NADPH oxidase in the drug-induced ROS production.

To confirm the intermediary role of PKCδ in OSU-2S's antiproliferative effect, the inventors assessed the effect of shRNA-mediated PKC knockdown on the viability and caspase-3 activity of drug-treated HCC cells. Hep3B cells were transfected with plasmids encoding shRNA against PKCδ, followed by clonal selection, which yielded two stable clones expressing different residual levels of PKCδ (FIG. 4C, upper panel). This shRNA knockdown was highly specific as no cross-silencing of the other PKC isozymes examined (α, ε, and ζ) was noted. As shown, these two stable clones provided differential protection against the antiproliferative effect of OSU-2S and FTY720 (central panel). Moreover, silencing of PKC expression suppressed the ability of OSU-2S to enhance caspase-3 activity (lower panel).

Figure 5:
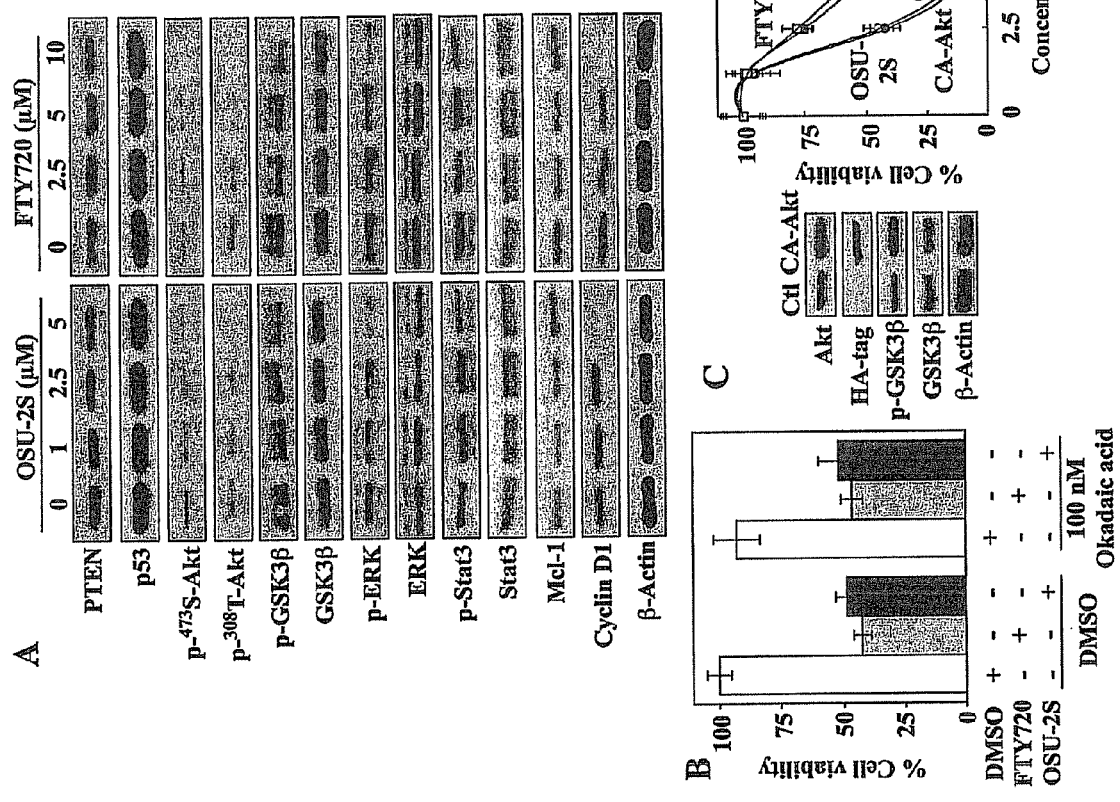
FIG. 5 provides graphs and data providing evidence that refutes the involvement of protein phosphatase 2A, PTEN, and Akt as targets for OSU-2S. Section (A) shows the Western blot analysis of the dose-dependent effects of OSU-2S and FTY720 on the phosphorylation/expression levels of PTEN, p53, Akt, GSK3β, ERK, Stat3, Mcl-1, and cyclin D1 in Huh7 cells after 24 h of treatment. Section (B) shows the effect of okadaic acid (100 nM) on the antiproliferative activities of 5 µM FTY720 and 2.5 µM OSU-2S in Huh7 cells after 24 h of treatment. Columns, mean; bars, ±SD (n=6). Section (C) shows the effect of ectopic expression of constitutively active Akt (CA-Akt) on the sensitivity of Huh7 cells to FTY-720- and OSU-2S-induced suppression of cell viability. Left, Western blot analysis of the expression level of Akt, HA-tag, p-GSK3β, and GSK3β in a stable CA-Akt-overexpressing clone versus untransfected Huh7 cells. Right, effect of FTY720 and OSU-2S on the viabilities of untransfected Huh7 cells (Ctl) and stable CA-Akt-overexpressing clones. Points, mean; bars, ±SD (n=6).

Evaluation of other potential mechanisms. Besides PKCδ, several distinct mechanisms have been proposed for the proapoptotic effects of FTY720 in different cancer cell systems, including induction of PTEN and p53 expression, activation of protein phosphatase $(PP)_2A$ and downregulation of Mcl-1, and downregulation of p-Akt and cyclin D1. To discern these possible mechanisms, the inventors examined the expression/functional status of various markers pertinent to these pathways in drug-treated Huh7 cells. Western blot analysis indicates that neither OSU-2S nor FTY720 had an appreciable effect on the expression levels of PTEN, p53, or Mcl-1 (FIG. 5A). Moreover, the involvement of PP2A was refuted by the inability of okadaic acid to protect cells from OSU-2S- or FTY720-induced cell death (FIG. 5B), even though OSU-2S and FTY720 modestly decreased the phosphorylation of various PP2A target proteins, including Thr-308- and Ser-473-Akt, ERK, and, to a lesser extent, Stat3 (FIG. 5A). As Huh7 cells exhibited low levels of p-Akt due to functional PTEN (7), this drug-induced Akt dephosphorylation was confirmed by parallel decreases in p-GSK3β levels accompanied by reduced cyclin D1 expression. To assess the role of Akt, the inventors investigated the effect of ectopic expression of a constitutively active form of Akt ($Akt^{T308D/S473D}$) on OSU-2S-induced cell death. The overexpression of CA-Akt, as evidenced by HA tag expression and increased GSK3β phosphorylation, did not confer any protection against FTY720- or OSU-2S-induced cell death (FIG. 5C).

Figure 6:
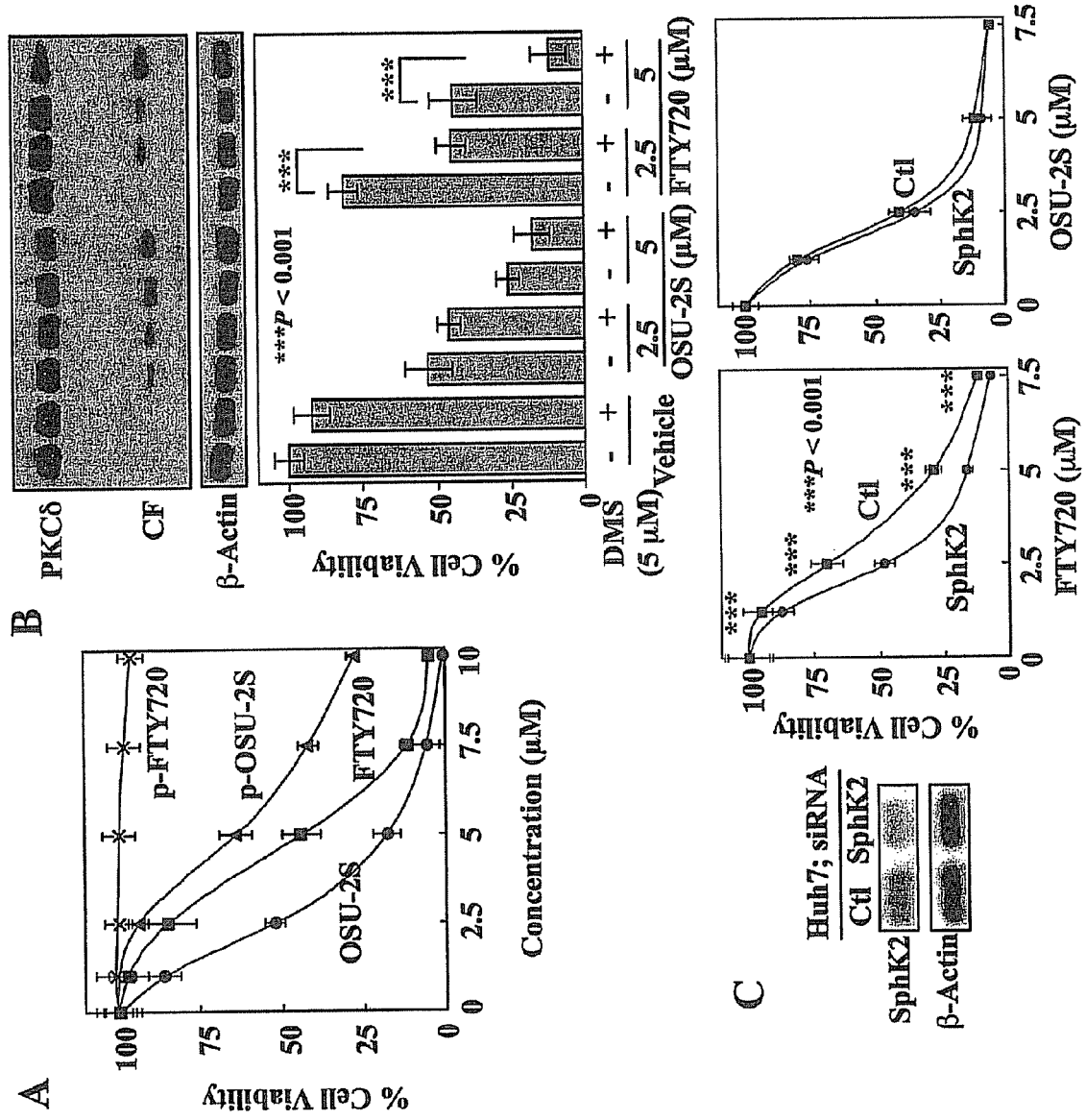
FIG. 6 provides graphs and data providing evidence that SphK2-mediated phosphorylation of FTY720 may underlie its lower antiproliferative potency relative to OSU-2S. Section (A) provides MTT assays of the dose-dependent suppressive effects of OSU-2S, phospho (p)-OSU-2S, FTY720, and p-FTY720 on the viability of Huh7 cells after 24 h of treatment. Points, mean; bar, +SD (n=6). Section (B) shows the effect of N,N-dimethylsphingosine (DMS, 5 µM), a pharmacological inhibitor of sphingosine kinase-2 (SphK2), on the dose-dependent activation of PKCδ (upper) and suppression of cell viability (lower) by OSU-2S versus FTY720 in Hep3B cells. Columns, mean; bars, ±SD (n=6). Section (C) shows the effect of siRNA-mediated knockdown of SphK2 expression on the sensitivity of Huh7 cells to the antiproliferative effects of FTY720 and OSU-2S. Left, expression levels of SphK2 in cells transfected with SphK2 siRNA or scrambled siRNA (Ctl). Right, knockdown of SphK2 expression enhances the effect of FTY720, but not OSU-2S, on cell viability. Points, mean; bars, ±SD (n=6).

The lower antiproliferative potency of FTY720 relative to OSU-2S is, in part, attributable to SphK2-mediated metabolic inactivation. Although SphK2-mediated phosphorylation of FTY720 is required for its effect on SP receptors and consequent immune modulation, evidence suggests that this phosphorylation represents a metabolic inactivation of its ability to elicit intracellular apoptosis signaling as p-FTY720 lacks in vitro efficacy in suppressing HCC cell viability (FIG. 6A). The inventors have shown above (FIG. 1B) that OSU-2S is not a substrate of SphK2; thus, it is not subject to phosphorylating inactivation. Consistent with this premise, synthetic p-OSU-2S retained partial antitumor activity, in contrast to p-FTY720 (FIG. 6A).

Consequently, the inventors hypothesize that SphK2-mediated phosphorylation underlies the lower antiproliferative activity of FTY720 and that inhibition of SphK2 activity would enhance its anticancer activity in HCC cells. This premise was supported by the potentiating effect of the SphK2 kinase inhibitor N,N-dimethylsphingosine (DMS) (5 µM) on FTY720-induced PKCδ activation and inhibition of Hep3B cell viability (FIG. 6B). DMS alone had no appreciable activity on either marker, but when combined with FTY720, achieved effects on PKCδ activation and cell viability equivalent to those of OSU-2S as a single agent at the same concentration. Consistent with the finding that OSU-2S is not a substrate of SphK2, this enhanced effect was not noted in cells co-treated with DMS and OSU-2S.

The finding described above was further confirmed by siRNA-mediated silencing of SphK2 expression in FTY720-treated Huh7 cells. Similar to the effect of pharmacological inhibition, knockdown of SphK2 expression significantly increased the antiproliferative activity of FTY720 (P<0.001) to a level comparable to that of OSU-2S. This sensitizing effect, however, was not observed with OSU-2S (FIG. 6C). These findings suggest that the difference in antitumor potencies of OSU-2S and FTY720 was attributable to differences in their susceptibility to SphK2-mediated phosphorylation.

Figure 7:
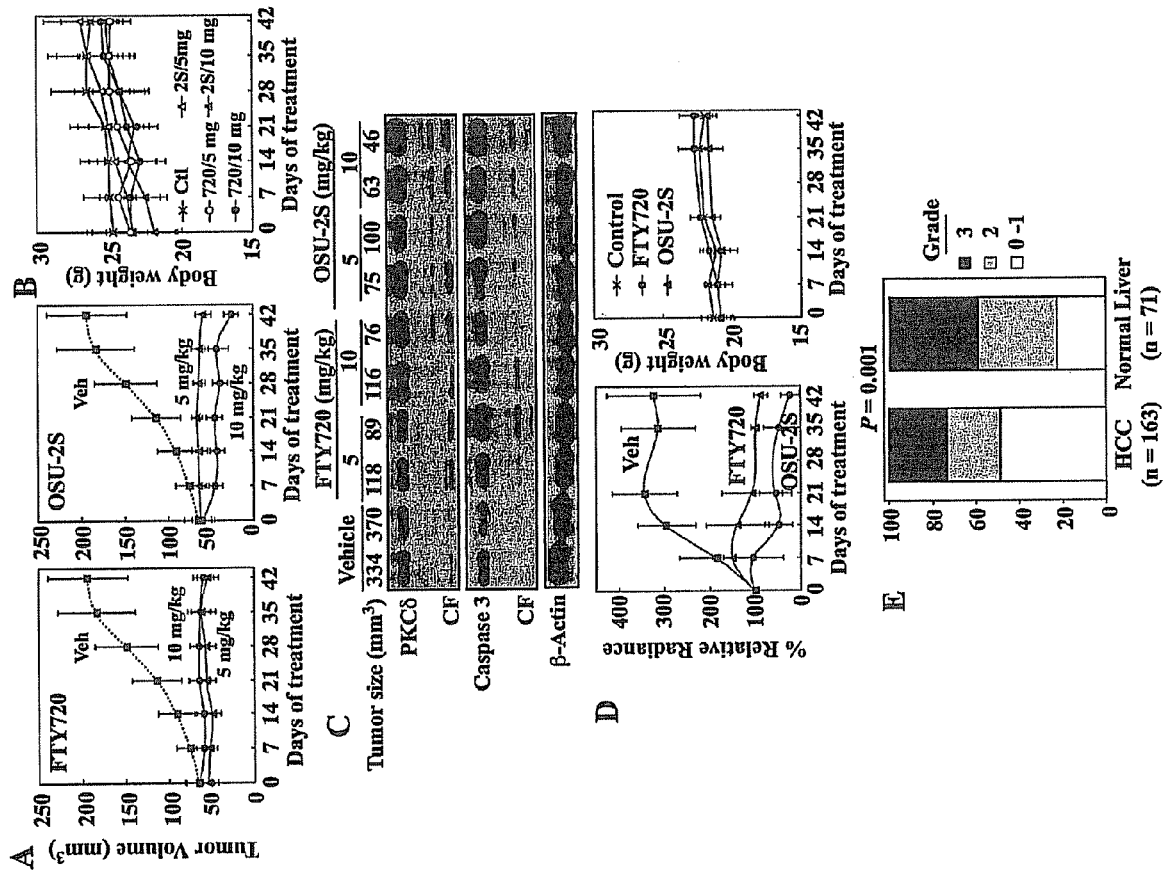
FIG. 7 provides graphs and data showing the In vivo efficacies of OSU-2S versus FTY720 in ectopic and orthotopic xenograft models of HCC tumor growth. Section (A) shows the effects of FTY720 (left) and OSU-2S (right) on the growth of subcutaneous Hep3B tumors in athymic nude mice. Mice bearing established Hep3B tumors were treated with FTY720 or OSU-2S at 5 or 10 mg/kg via daily i.p. injection for 42 days. Veh, vehicle. Points, mean; bars, ±SD (n=8). Section (B) shows that treatments had no effect on the body weights of ectopic tumor-bearing mice. Ctl, vehicle-treated control; 720, FTY720; 2S, OSU-2S. Points, mean; bars, +S.D. (n=8). Section (C) shows the Western blot analysis of intratumoral biomarkers of drug activity in the homogenates of two representative subcutaneous Hep3B tumors from each treatment group. CF, catalytic fragment. Section (D) Left panel, shows the effects of FTY720 and OSU-2S on the growth of established orthotopic luciferase-expressing Hep3B tumors in athymic nude mice. Tumor burden was determined by weekly measurements of bioluminescence. The mice were treated with FTY720 or OSU-2S at 5 mg/kg or with the vehicle via daily i.p. injection for 42 days. Veh, vehicle. Points, mean; bars, ±S.D. (n=3). Right panel, treatments had no effect on the body weights of mice bearing orthotopic tumors. Points, mean; bar, ±S.D. (n=3). Section (E) provides immunohistochemical analysis of PKCδ expression levels in HCC (n=163) and normal human liver tissues (n=71) on a tissue microarray. Intensities of immunohistochemical staining were semi-quantitatively scored as follows: 0, negative; 1, weak; 2, moderate; 3, strong. Fisher's exact test shows a significant difference (P=0.001) between the HCC and normal liver tissues with respect to the proportions of tissues that are PKCδ-positive.

OSU-2S exhibits potent in vivo efficacy in suppressing HCC tumor growth in two different murine models. The in vivo antitumor efficacy of OSU-2S was evaluated vis-à-vis FTY720 in both ectopic and orthotopic Hep3B tumor xenograft models. Athymic nude mice bearing established subcutaneous Hep3B tumors were treated by i.p. injection once daily with OSU-2S or FTY720 at 5 and 10 mg/kg, or with vehicle only. As shown, both agents at 5 g/kg completely suppressed ectopic Hep3B tumor growth in comparison to the vehicle control (P<0.001) (FIG. 7A). While no dose dependency in the tumor-suppressive response to FTY720 was noted, OSU-2S at 10 mg/kg reduced tumor volume by more than 50% by the end of 42-day treatment period. Examination of intratumoral biomarkers of drug activity in Hep3B tumor tissue homogenates showed that PKCδ and caspase-3 were activated in the tumors from FTY720- and OSU-2S-treated mice, confirming the in vitro mechanistic findings.

The daily administration of both drugs was apparently well tolerated as the mice showed no overt signs of toxicity and no loss of body weight (FIG. 7B). Moreover, no histologic lesions consistent with toxic injury were observed in any of the organs examined microscopically, with the exception of mesentery and mesenteric blood vessels. Specifically, of the six mice per group examined histologically, three that received 5 mg/kg FTY720 and all that received 10 mg/kg FTY720 and either dose of OSU-2S had evidence of abdominal adhesions with varying amounts of peritonitis. In some of these affected mice, the inflammation exhibited varying degrees of angiocentricity with vasculitis in some cases. The FTY720-treated mice exhibited minimal to mild lymphopenia, while lymphocyte levels in all OSU-2S-treated mice were normal. Drug-treated mice also exhibited mild to moderate elevations in neutrophils that may have been associated with the aforementioned peritonitis. Minimal to mild elevations in total bilirubin, AST and ALT were observed in some of the drug-treated mice, but are likely of no clinical significance and there were no corresponding histologic lesions in the livers of these mice.

To confirm that the in vivo tumor-suppressive activities of FTY720 and OSU-2S described above could also occur in the context of a relevant tumor microenvironment, in vivo efficacy was assessed in an orthotopic xenograft model. Hep3B-luc cells were injected into the livers of athymic nude mice and establishment of orthotopic tumors was confirmed by bioluminescent imaging. Mice were treated via i.p. injection with OSU-2S and FTY720 at 5 g/kg daily or with the vehicle for 42 days. As shown in FIG. 7D, orthotopic Hep3B-luc tumors in vehicle-treated mice exhibited growth during the first 21 days of treatment, after which it reached a plateau. Tumors in FTY720-treated mice showed a gradual rise in bioluminescent intensities over the first week of treatment, but, by three weeks, the drug suppressed mean tumor burden to the original level. Relative to FTY720, OSU-2S exhibited a higher tumor-suppressive potency in this orthotopic tumor model, achieving 80% reduction in bioluminescent intensity at the end of treatment. Both treatments were well tolerated as indicated by stable body weights (FIG. 7D, right panel).

PKCδ expression in human HCC versus non-neoplastic human liver tissues. Although downregulation of PKCδ expression has been reported in many cancer types, including squamous cell carcinoma (D'Costa et al., Oncogene, 25, 378-386 (2006)), urinary bladder carcinoma (Varga et al., Eur Urol, 46, 462-465 (2004)), and endometrial cancer (Reno et al., Hum Pathol, 39, 21-29 (2008)), information regarding the expression of this proapoptotic kinase in HCC is lacking. Thus, the inventors used a TMA to evaluate PKCδ expression in 163 human HCC and 71 non-neoplastic liver tissue samples. The data show a lower expression level of PKCδ in HCC relative to non-neoplastic liver (P=0.001) (FIG. 7E).

Discussion

Considering the translational potential of FTY720 as a therapeutic agent for HCC, it is desirable to dissociate the SIP receptor agonist activity of FTY720 from its antitumor effects to avoid untoward side effects associated with immunomodulatory therapies. The identification of OSU-2S provides a proof-of-concept that these two pharmacological activities could be separated via structural modifications to develop novel antitumor agents with a unique mode of action. In contrast to FTY720, OSU-2S lacks significant effects on S1P1 receptor internalization in Huh7 cells and T lymphocyte homing in immunocompetent mice. Though devoid of immunosuppressive activity, OSU-2S exhibits twofold higher in vitro antiproliferative efficacy relative to FTY720 against HCC cells. Moreover, like FTY720, this antitumor activity is mediated, in part, through the activation of PKC signaling. PKC plays an intriguing role in regulating apoptosis, eliciting either proapoptotic or antiapoptotic effects in a cell type- and context-specific manner (Jackson et al., FASEB J, 18:627-636 (2004)). In this study, we demonstrated that OSU-2S shared the ability of FTY720 to mediate PKCδ-dependent apoptosis through ROS production, and that caspase-3 not only represents a downstream effector of PKCδ, but also provides a positive feedback by facilitating PKCδ activation via proteolytic cleavage. The finding that DPI rescued cells from drug-induced PKC activation and cell death suggests that NADPH oxidase is involved in drug-induced ROS production.

This unique mechanism might underlie the high potency of OSU-2S and FTY720 in mediating apoptotic death in HCC cells as somatic GST-π gene silencing is a frequent feature of HCC leading to low antioxidant capacity (Tchou et al., Int J Oncol, 16, 663-676 (2000)). This premise was corroborated by the ability of siRNA-induced repression of GST-π to sensitize PLC5 cells, which exhibit high levels of endogenous GST-π, to OSU-2S- and FTY720-mediated growth inhibition.

In contrast to the gain of S1P receptor agonist activity by FTY720 after SphK2-mediated phosphorylation, metabolic transformation of FTY720 to its phosphate derivative results in the loss of its antitumor activity. Since FTY720 is gradually phosphorylated and secreted, this inactivation/sequestration may explain the lower antiproliferative potency of FTY720 relative to OSU-2S, which is not phosphorylated by SphK2. Indeed, the data show that the suppression of SphK2 activity by pharmacological inhibition or knockdown of gene expression enhanced the antitumor activity of FTY720 to the same level as that of OSU-2S.

As a single agent in vivo, OSU-2S exhibited high tumor-suppressive activity against both subcutaneous and intrahepatic HCC xenograft tumors through the activation of PKCδ and caspase-dependent apoptosis without overt toxicity. The abdominal adhesions and varying degrees of peritonitis observed in drug-treated mice were likely a response to the chronic irritation associated with repeated i.p. injections of the agents. The angiocentric inflammation noted in the mesenteric vasculature of some drug-treated mice may represent either a localized hypersensitivity reaction to the compounds or a localized vascular toxicity, the significance of which is unclear.

Evaluation of PKCδ expression in a human TMA revealed lower expression levels PKCδ in HCC than in nonmalignant liver tissues, suggesting that the down-regulated expression of this proapoptotic kinase in HCC may provide survival advantages. This premise is supported by the inventors' finding that shRNA-mediated knockdown of PKCδ reduced the sensitivity of Huh7 cells to the antiproliferative effects of OSU-2S. From a clinical perspective, the expression levels of PKCδ and GST-π represent two key determinants for cellular sensitivity to OSU-2S, and thus may be useful as criteria for selecting patients to receive OSU-2S therapy; i.e., OSU-2S would benefit HCC patients with moderate to high PKCδ and low GST-π expression.

In summary, the inventors report the development of OSU-2S, a non-immunosuppressive analogue of FTY720. Unlike FTY720, OSU-2S is not subject to SphK2-mediated phosphorylation and thus exhibits higher antitumor potency than FTY720. These findings, along with the potent in vivo tumor-suppressive activity, support the translational potential of OSU-2S as a component of therapeutic strategies for advanced HCC, for which systemic therapies have been largely unsuccessful.

Example 3

Antitumor Effects of OSU-2S in Chronic Lymphoid Leukemia (CLL) Cells

Antitumor and other effects of OSU-2S were also evaluated in Chronic Lymphoid Leukemia cells. OSU-2S cytotoxicity in primary CLL cells is measured at 24 hrs by staining for Annexin V and Propidium Iodide using Flow cytometer. The number of live cells (stained negative for both the stains) were normalized to untreated control. Fludarabine metabolite (2-Fara) was used as a control. Cells treated with 8 μM OSU-2S showed about 30% growth, as compared with 100% growth for untreated and control cells.

Figure 9:
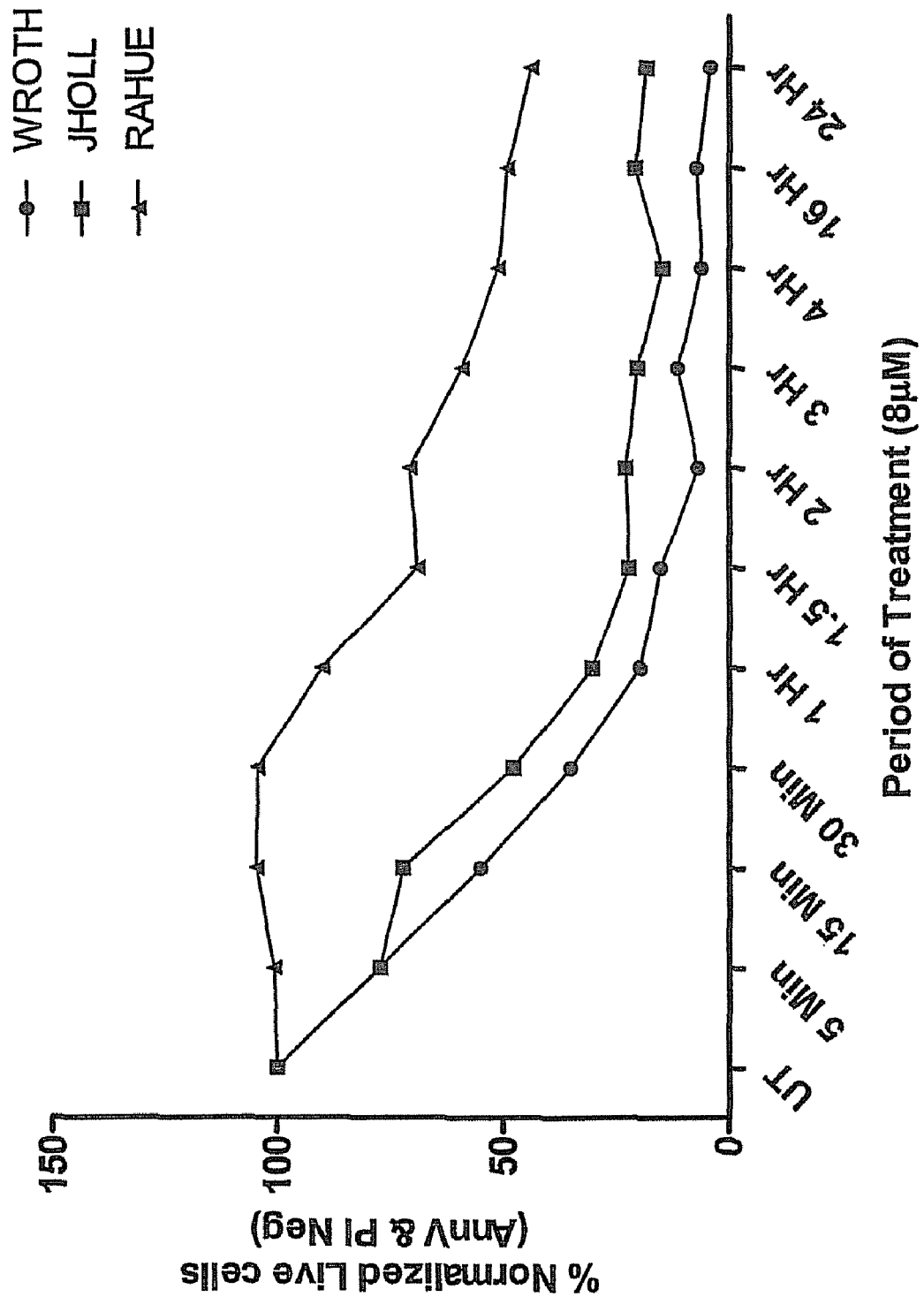
FIG. 9 provides a graph showing the time dependent OSU-2S cytotoxicity in primary CLL cells. The effect of OSU-2S was evaluated in 3 different CLL cell lines (WROTH<JHOLL, and RAHUE) over a 24 hour period.

The effect of OSU-2S was evaluated in 3 different CLL cell lines (WROTH<THOU, and RAHUE) over a 24 hour period, as shown in FIG. 9. Time dependent OSU-2S cytotoxicity in primary CLL cells was measured by treating the cells with OSU-2S (8 μM) for indicated period of time and washed and cultured in the fresh media for 24 hr. The number of live cells stained negative for Annexin V and Propidium Iodide were measured at 24 hrs by using Flowcytometer and normalized to untreated control. The results show that all of the CLL cell lines treated with OSU-2S exhibited a decreased number live cells over time, showing that OSU-2S cytotoxicity is time dependent in CLL.

The ability of OSU-2S to induce PP2A (Serine/Threonine Phosphatase 2A) activity in primary CLL cells was measured at 24 hrs by a functional enzymatic assay. Lysates made from OSU-2S 8 μM treated cells are used to immunoprecipitate PP2Ac which was then used as an enzyme to cleave the specific phosphor-peptide substrate in the functional assay. The cleaved free phosphates were measured by adding malachite green detection solutions and measuring the absorbance at A650 nm. Ramos cells were also included, and FTY720 was used as the control. Whereas untreated cells showed an absorbance of about 0.07, FTY720 and OSU-2S cells showed an absorbance of about 0.20, showing increased PP2A activity.

The induction of Reactive Oxygen Species (ROS) in CLL cells by OSU-2S was detected by staining OSU-2S 8 μM treated CLL cells with dihyroethidium. The ROS in the cells oxidizes DHE to ethidium staining the nucleus with a bright red fluorescence detected by flow cytometer. A hydrogen peroxide solution was used as a control. Untreated cells showed a DHE positive cell % of about 40% while OSU-2S treated cells showed a DHE positive cell value % of about 70%, indicating the OSU-2S induces ROS in CLL.

CD37 activation and OSU-2S produced enhanced cytotoxicity in CLL cells, as detected by flow cytometer at 24 hr. in CLL cells treated with CD37 antibody and cross linker or OSU-2S 8 μM or with both are stained for Annexin V and propidium iodide at 24 hr. The number of live cells stained negative for both the stains for displayed. CD37 and αFC showed about 50% live cells, OSU-2S showed about 30% live cells, and OSU-2S, together with CD37 and αFC showed about 20% live cells.

Western blot analysis as carried out to further observe the effects of OSU-2S in CLL cells. First, PARP cleavage was shown to occur in OSU-2S treated CLL cells. OSU-2S in CLL activates caspase, as evidenced by cleavage of poly (ADP-ribose) polymerase (PARP). Jurkat cell with or without UV irradiation were included as controls. OSU-2S treated cells showed higher levels of PARP at both 24 and 48 hours, as compared with untreated CLL cells. OSU-2S was also shown to activate caspase 3 in CLL cells. Both OSU-2S and 2-FaraA treated cells showed caspase 3 cleaved products at about 16-18 kD at 24 and 48 hours. Finally, OSU-2S activates caspase 9 in CLL. Both OSU-2S and 2-FaraA treated cells showed caspase 9 cleaved products at about 30-34 kD.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing possible mechanisms through with the compounds of the invention are effective, the inventors are not bound by theories described herein. The invention is not limited to the exact details shown and described, for variations obvious to one skilled in the art will be included within the invention defined by the claims.

What is claimed is:

1. A compound of formula I:

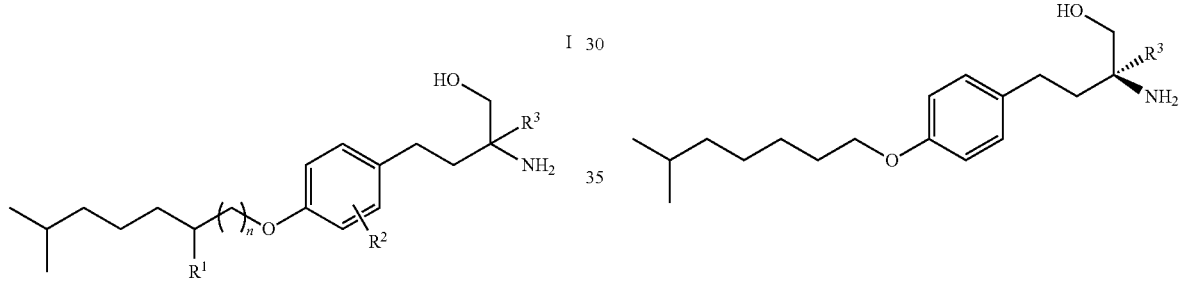

wherein $R^1$ is independently selected from the group consisting of hydrogen, methyl. methoxy, and hydroxyl;
$R^2$ is independently selected from the group consisting of hydrogen, methoxy, and hydroxyl;
$R^3$ is independently selected from the group consisting of alkyl and cyclo-alkyl; and
n is independently selected from 0 to 6.

2. The compound of claim 1, wherein $R^1$ is hydrogen.
3. The compound of claim 2, wherein n is from 0 to 3.
4. The compound of claim 1, wherein $R^1$ is methyl.
5. The compound of claim 4, wherein n is from 0 to 3.
6. The compound of claim 1, wherein $R^2$ is hydrogen.
7. The compound of claim 1, wherein $R^2$ is 2-methoxy.
8. The compound of claim 1, wherein $R^2$ is 3-methoxy.
9. The compound of claim 1, wherein $R^2$ is 2-hydroxy.
10. The compound of claim 1, wherein $R^2$ is 3-hydroxy.
11. The compound of claim 1, wherein $R^3$ is propyl.
12. The compound of claim 1, wherein $R^3$ is isopropyl.
13. The compound of claim 1, wherein $R^3$ is isobutyl.
14. The compound of claim 1, wherein $R^3$ is cyclopropyl methyl.
15. The compound of claim 1, wherein $R^3$ is cyclobutyl methyl.
16. The compound of claim 1, wherein the compound has the structure:

* * * * *